United States Patent
Li et al.

(10) Patent No.: US 11,021,753 B2
(45) Date of Patent: Jun. 1, 2021

(54) MUTANT GENES RELATED TO DRUG RESISTANCE AND RELAPSE OF ACUTE LYMPHOBLASTIC LEUKAEMIA AND A USE THEREOF

(71) Applicant: SHANGHAI CHILDREN'S MEDICAL CENTER, SHANGHAI JIAO TONG UNIVERSITY SCHOOL OF MEDICAL, Shanghai (CN)

(72) Inventors: Benshang Li, Shanghai (CN); Hui Li, Shanghai (CN); Shengyue Wang, Shanghai (CN); Binbing Zhou, Shanghai (CN)

(73) Assignee: SHANGHAI CHILDREN'S MEDICAL CENTER, SHANGHAI JIAO TONG UNIVERSITY SCHOOL OF MEDICAL, Shanghai (CN)

( * ) Notice: Subject to any disclaimer, the term of this patent is extended or adjusted under 35 U.S.C. 154(b) by 134 days.

(21) Appl. No.: 15/551,583

(22) PCT Filed: Feb. 18, 2016

(86) PCT No.: PCT/CN2016/073906
§ 371 (c)(1),
(2) Date: Aug. 16, 2017

(87) PCT Pub. No.: WO2016/131420
PCT Pub. Date: Aug. 25, 2016

(65) Prior Publication Data
US 2019/0093171 A1  Mar. 28, 2019

(30) Foreign Application Priority Data
Feb. 17, 2015 (CN) .......................... 201510086558.0
Feb. 17, 2015 (CN) .......................... 201510086559.5

(51) Int. Cl.
| | |
|---|---|
| C12N 15/62 | (2006.01) |
| C07K 14/435 | (2006.01) |
| C12Q 1/6886 | (2018.01) |
| C12N 15/113 | (2010.01) |
| C12N 9/12 | (2006.01) |
| G01N 33/50 | (2006.01) |
| G01N 33/574 | (2006.01) |

(52) U.S. Cl.
CPC ......... C12Q 1/6886 (2013.01); C12N 9/1235 (2013.01); C12N 15/113 (2013.01); C12Y 207/06001 (2013.01); G01N 33/5011 (2013.01); G01N 33/57426 (2013.01); C12N 2310/14 (2013.01); C12N 2310/20 (2017.05); C12N 2310/531 (2013.01); C12Q 2600/106 (2013.01); C12Q 2600/136 (2013.01); C12Q 2600/156 (2013.01); G01N 2800/50 (2013.01)

(58) Field of Classification Search
None
See application file for complete search history.

(56) References Cited

U.S. PATENT DOCUMENTS

| | | | |
|---|---|---|---|
| 2010/0004253 A1 | 1/2010 | Aziz et al. | |
| 2011/0092436 A1* | 4/2011 | Mandler | C07K 7/06 514/17.7 |

FOREIGN PATENT DOCUMENTS

| | | |
|---|---|---|
| CN | 101541977 A | 9/2009 |
| CN | 105985960 A | 10/2016 |
| CN | 105986023 A | 10/2016 |
| WO | WO-2009/084753 A1 | 7/2009 |
| WO | WO-2014/116704 A1 | 7/2014 |

OTHER PUBLICATIONS

Katayama et al, Science 309 (5740): 1564 (2005).*
The DNA Story, Watson et al, W.H Freeman and Co. San Francisco, 1981, p. 547.*
Charles G Mulighan, Mutant PRPS1: a new therapeutic target in relapsed acute lymphoblastic leukemia, Nature medicine 21(6):553-554, Jun. 4, 2015.
International Search Report and Written Opinion with English translation issued in corresponding application No. PCT/CN2016/073906 dated May 23, 2016.
Li Benshang et al., Negative feedback—defective PRPS1 mutants drive thiopurine resistance in relapsed childhood ALL, Nature Medicine 21(6) : 563-571, May 11, 2015.

(Continued)

Primary Examiner — James Martinell
(74) Attorney, Agent, or Firm — Foley & Lardner LLP

(57) ABSTRACT

This disclosure provides mutant genes related to drug resistance and relapse of acute lymphoblastic leukaemia (ALL) and a use thereof, treatment or prevention of drug resistance and relapse of ALL and a use thereof, a use of compound Lometrexol and related inhibitors targeting GART and AITC in prevention and treatment of drug resistance and relapse of ALL, and a kit for evaluation of the risk of drug resistance and relapse of ALL. The mutation gene is a mutant gene of PRPS1. The drug acts on enzymes in purine synthesis pathway and reduces drug resistance and relapse by decreasing the concentration of hypoxanthine. The kit comprises reagents for lysis of sample cells and an instruction. The invention provides a powerful technical means and support for the prevention and treatment of drug resistance and relapse of ALL.

9 Claims, 13 Drawing Sheets
Specification includes a Sequence Listing.

(56) References Cited

OTHER PUBLICATIONS

Li Jianzhong, Yuan Huijan, Han Dongyi, PRPS1 gene mutation and hereditary deafness, Chinese Journal of Otology, 8(1):57-62, with English translation, (2010).

Li Zhongqin, Xu Xiaoping, Wang Wu, Determination of Hypoxanthine in Serum by Dual Enzyme Coupled Catalytic Spectrophotometry, Spectroscopy and Spectral analysis, 28(9):2169-2172, Sep. 2008, with English translation.

Wang, Hai, et al., "Determination of IMP in poultry muscle by HPLC", Journal of Southwest University for Nationalities, Natural Science Edition, vol. 39, issue 5, Sep. 2013, pp. 667-670 (with English abstract only).

First Office Action and Search Report issued in corresponding Chinese Application No. 201510086558.0 dated Mar. 21, 2019 issued by the State Intellectual Property Office of People's Republic of China, (17 pages).

Arjan P.M. de Brouwer, et al.,"PRPS1 Mutations: Four Distinct Syndromes and Potential Treatment," The Journal of American of Human Genetics, 86, Apr. 9, 2010, pp. 506-518.

Gabriele Escherich, et al., Doxorubicin or Daunorubicin Given Upfront in a Therapeutic Window are Equally Effective in Children With Newly Diagnosed Acute Lymphoblastic Leukemia. A Randomized Comparison in Trial CoALL 07-03, Pediatr Blood Cancer, 2013, 60:254-257.

First Office Action and corresponding search report issued in corresponding Chinese application No. 201510086559.5 dated Mar. 9, 2020.

Second Office Action issued in corresponding Chinese application No. 201510086559.5 dated Aug. 26, 2020.

\* cited by examiner

MUTANT GENES RELATED TO DRUG RESISTANCE AND RELAPSE OF ACUTE LYMPHOBLASTIC LEUKAEMIA AND A USE THEREOF

CROSS-REFERENCE TO RELATED APPLICATIONS

This application is a U.S. National Stage Application of International Patent Application No. PCT/CN2016/073906, filed on Feb. 17, 2016, which claims priority to Chinese Patent Application No. CN201510086559.5, filed on Feb. 17, 2015 and Chinese Patent Application No. CN201510086558.0, filed on Feb. 17, 2015, the contents of each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Aug. 20, 2018, is named 116487-0200.txt and is 15.1 KB in size.

FIELD OF THE INVENTION

This invention relates to the field of biomedicine, and particularly, to a mutant gene related to drug resistance and relapse in acute lymphoblastic leukemia and a use thereof.

BACKGROUND OF THE INVENTION

Childhood Acute Lymphoblastic Leukemia (ALL) is a common hematological malignancy in childhood, and it is one of the primary reasons for the death of children in China. Although the treatment and prognosis of children with ALL has been improved significantly over the past few decades, there is still 15% to 20% of children will relapse, and the cure rate is less than 40% once it relapses. Relapse has been the primary reason in the failure and death of childhood ALL. The problem of relapse has become the hotspot and focus of domestic and foreign research on childhood ALL.

In the treatment of childhood ALL, chemotherapy is one of the major means of inducing remission and post-remission therapy. Currently, chemotherapy drugs commonly used in clinical are usually the nucleotide analogues which interrupt the synthesis of DNA or RNA, hence leading to DNA damage and inducing tumor cell apoptosis. In the stage of inducing remission of Childhood ALL, 90% of patients will be relieved using the combination chemotherapy with large dose of drug. After that, the treatment will be maintained using low dose of chemotherapeutic drugs. During maintenance of treatment, oral administration of 6-mercaptopurine (6-MP) or 6-thioguanine (6-TG) has been used, and the relapse occurs accumulatively only when tumor cells tolerate the effects of 6-MP/6-TG. Recently, the samples of leukemia patients with drug resistance and relapse was detected using next-generation sequencing by Adolfo Ferrando and William L Carroll's team and mutations in the 5'-nucleotidase II (NT5C2) gene encoding enzymes were found related to the metabolism of 6-mercaptopurine (6-MP) and 6-thioguanine (6-TG) in relapsed ALL cells. The mutation rate is about 10% in relapsed ALL cells. The resistance and relapse of childhood ALL cannot be explained by a single base mutation of a gene. Identifying the genetic variation associated with relapse remains the focus and difficulty in the research of drug resistance and relapse in childhood ALL, and accordingly, the means of detection and treatment are relatively deficient.

PRPS1 gene encoding Phosphoribosyl Pyrophosphate Synthetase is the first rate-limiting enzyme for intracellular purine metabolic synthesis pathway. PRPS1 catalyzes the reaction of 5-phosphate ribose and ATP to produce AMP and PRPP (5-phosphoribosyl-1-pyrophosphate). PRPP undergoes a series of enzymatic reactions to produce hypoxanthine nucleotide (IMP), and IMP is further converted to raw materials for DNA and RNA synthesis, such as (d) ATP and (d) GTP. Excessive and extremely low content of intracellular PRPP can both cause abnormal of metabolic pathway that taken it as a substrate or regulator, and leading to the occurrence of the disease. Currently, it has been found that mutations in PRPS1 is associated with diseases, such as X-linked nonsyndromic sensorineural deafness (DFN2), X-linked Charcot-Marie-Tooth disease-5 (CMTX5) and the like. PRPS1 mutations contain gain of function mutations, such as D183H, A190V, D52H and the like, and loss of function mutations, such as A87T, M115T, I290T and the like. However, PRPS1 mutations have not been found in tumors so far.

Lometrexol, of which the CAS Number is 106400-81-1, having the molecular formula $C_{21}H_{25}N_5O_6$ and molecular weight 443.45. The structural formula is as follows:

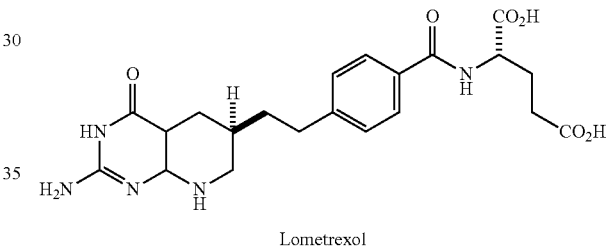

Lometrexol

Lometrexol is an antifolate that inhibits the activity of glycine amide acetyltransferase (GART) after being transported into the cells by reductive folate carrier and folate receptor. GART is the key enzyme in the purine de novo synthesis pathway. As a potential antitumor drug, it is also effective against some cell lines that are resistant to other antineoplastic drugs. Currently, Phase II clinical trial of the drug in foreign countries has been completed, but so far there is no report on the drug in the prevention and treatment for drug resistance and relapse of ALL.

SUMMARY OF THE INVENTION

The present invention solves the technical problem that it provides a group of mutant genes related to drug resistance and relapse of ALL and a use thereof in evaluating risk of drug resistance and relapse of childhood ALL. The present invention also provides drug targets for preventing and treating drug resistance and relapse of ALL, RNA drugs for treating drug resistance and relapse of ALL, and inhibitors of one or more enzymes in purine de novo synthesis pathway in preparation of drugs for preventing or treating drug resistance and relapse of ALL. Also provides a kit for evaluating the risk of drug resistance and relapse of ALL and a use thereof for evaluating the risk of drug resistance and relapse of childhood ALL. The present invention is of important guiding significance for gene diagnosis and individualized treatment in subsequent early clinical relapse.

The technical solutions for solving the above-mentioned technical problems in present invention are as follows:

In a first aspect, the present invention provides a use of PRPS1 as a gene marker of drug resistance and relapse of ALL.

The present invention also provides a PRPS1 mutant, wherein the PRPS1 mutant is formed by a substitution mutation at any one of the following positions in the sequence shown in SEQ ID No. 2 in the Sequence Listing; said substitutions are as follows: serine was substituted by threonine at position 103, serine was substituted by asparagine at position 103, asparagine was substituted by serine at position 144, lysine was substituted by asparagine at position 176, aspartic acid was substituted by glutamic acid at position 183, alanine was substituted by threonine at position 190, leucine was substituted by phenylalanine at position 191, threonine was substituted by serine at position 303, valine was substituted by alanine at position 53, isoleucine was substituted by valine at position 72, cysteine was substituted by serine at position 77, aspartic acid was substituted by glycine at position 139, tyrosine was substituted by cysteine at position 311, serine was substituted by isoleucine at position 103, asparagine was substituted by aspartic acid at position 114 or glycine was substituted by glutamic acid at position 174. The mutant with serine being substituted by threonine at position 103 is shown as S103T in the present invention. The other mutants are described in same manner as set forth above, followed by S103N, N144S, K176N, L191F, D183E, A190T, T303S, V53A, I72V, C77S, D139G, Y311C, S103I, N114D or G174E.

The present invention provides a PRPS1 mutant gene that encoded a PRPS1 mutant of the amino acid sequence as described above.

In present invention, the PRPS1 mutant gene may be a conventional mutant gene in the art, which is able to encode the PRPS1 mutant of the above-mentioned amino acid sequence due to codon degeneracy. Preferably, DNA sequence of the mutant gene is formed by making an amino acid substitution at any one of the following sites of SEQ ID No. 1 in Sequence Listing, the substitutions are as follows: G was substituted by C at position 308, G was substituted by A at position 308, A was substituted by G at position 431, G was substituted by C at position 528, C was substituted by G at position 549, G was substituted by A at position 568, G was substituted by C at position 573, C was substituted by G at position 908, T was substituted by C at position 158, A was substituted by G at position 214, G was substituted by C at position 230, A was substituted by G at position 416, A was substituted by G at position 932, G was substituted by T at position 308, A was substituted by G at position 340 or G was substituted by A at position 521.

The mutant with G being substituted by C at position 308 is abbreviated as G308C, and other substitutions are described similarly as set forth above, followed by G308A, A431G, G528C, C549G, G568A, G573C, C908G, T158C, A214G, G230C, A416G, A932G, G308T, A340G or G521A.

The present invention provides a recombinant vector comprising a PRPS1 mutant gene as described herein. Said recombinant vector is conventional in the art; preferably a prokaryotic expression vector or an eukaryotic expression vector capable of expressing the PRPS1 mutant gene; more preferably a lentiviral expression vector capable of expressing the PRPS1 mutant gene; most preferably GV303 lentiviral expression vector (Shanghai Genechem Co., Ltd). Preparation method of the eukaryotic expression vector is conventional in the art and preferably prepared by linearizing the lentiviral expression vector with restriction endonuclease, exchanging PCR products of PRPS1 mutant gene into the linearized lentiviral vector using In-Fusion™ PCR Cloning Kit from Clontech, and finally amplifying the recombinant vector by *Escherichia coli* TOP 10 to form a recombinant vector containing the PRPS1 mutant gene of the present invention.

The invention provides a transformant comprising the recombinant vector. The transformant is conventional in the art, as long as the recombinant vector can be stably self-replicated and the PRPS1 mutant gene of present invention can be efficiently expressed, preferably a prokaryotic or eukaryotic cells expressing the PRPS1 mutant gene of present invention, more preferably a eukaryotic cells expressing the PRPS1 mutant gene of present invention, most preferably a Reh cell line expressing the PRPS1 mutant gene of present invention. The preparation method of the transformant is conventional in the art, preferably the transformant is prepared by packaging the lentiviral expression vector expressing the PRPS1 mutant gene of the present invention as a lentivirus and infecting eukaryotic cells by the lentivirus, most preferably the transformant is prepared by co-transfecting GV303 lentiviral expression vector (Shanghai Genechem Co., Ltd) expressing the PRPS1 mutant gene of the present invention and virus-loaded helper plasmid into HEK293T cells to form a package of lentivirus and infecting the eukaryotic cells Reh by the lentivirus, and finally sorting cells having positive signal of green fluorescent using flow cytometry.

In the second aspect, the present invention provides a group of PRPS1 mutants library for evaluating the risk of drug resistance and relapse of ALL, and the group of PRPS1 mutants library comprises the following PRPS1 mutants: in the amino sequence of SEQ ID No. 2 in Sequence Listing, serine is replaced by threonine at position 103, serine is replaced by asparagine at position 103, asparagine is replaced by serine at position 144, lysine is replaced by asparagine at position 176, aspartic acid is replaced by glutamic acid at position 183, alanine is replaced by threonine at position 190, leucine is replaced by phenylalanine at position 191 or threonine is replaced by serine at position 303, namely S103N, N144S, K176N, L191F, D183E, A190T or T303S.

Preferably, the mutants library also comprises one or more following PRPS1 mutants and the amino sequence of mutant has the sequence of SEQ ID No. 2 in the Sequence Listing, while valine is replaced by alanine at position 53, isoleucine is replaced by valine at position 72, cysteine is replaced by serine at position 77, aspartic acid is replaced by glycine at position 139, tyrosine is replaced by cysteine at position 311, serine is replaced by isoleucine at position 103, asparagine is replaced by aspartic acid at position 114, glycine is replaced by glutamic at position 174 or glycine is replaced by valine at position 190, namely V53A, I72V, C77S, D139G, Y311C, S103I, N114D, G174E or A190V.

The present invention provides a group of PRPS1 mutant genes library for evaluating the risk of drug resistance and relapse of ALL, the PRPS1 mutant genes library comprises following PRPS1 mutant genes: as the nucleotide sequence shown in SEQ ID NO. 1 in the Sequence Listing, G is replaced by C at position 308, G is replaced by A at position 308, A is replaced by G at position 431, G is replaced by C at position 528, C is replaced by G at position 549, G is replaced by A at position 568, G is replaced by C at position 573, or C is replaced by G at position 908, namely G308C, G308A, A431G, G528C, C549G, G568A, G573C or C908G.

Preferably, the mutant genes library also comprises one or more following PRPS1 mutant genes: as the nucleotide sequence shown in SEQ ID No. 1 in the Sequence Listing, T is replaced by C at position 158, A is replaced by G at position 214, G is replaced by C at position 230, A is replaced by G at position 416, A is replaced by G at position 416, A replaced by G at position 932, G is replaced by T at position 308, A is replaced by G at position 340, G is replaced by A at position 521, or C is replaced by T at position 569, namely T158C, A214G, G230C, A416G, A932G, G308T, A340G, G521A or C569T.

The present invention provides a kit for evaluating the risk of drug resistance and relapse of ALL, wherein the kit comprises instruction and reagents for detecting a PRPS1 mutant gene in the mutant genes library of present invention.

The reagents can be any of conventional reagents for detecting PRPS1 mutations in the art, preferably, said reagents comprise one or more reagents selected from primers for amplification of PRPS1 gene exons, DNA polymerase, dNTP and Buffer.

The primers for amplifying PRPS1 gene exons are conventional primers for amplifying PRPS1 gene exons, preferably any nucleotide sequence of SEQ ID NOs. 3-16 in Sequence Listing.

Preferably, the detection kit also comprises reagents for extracting DNA from cells or tissue samples. The reagents for extracting DNA from cells or tissue samples are conventional in the art, preferably a protease, a saturated phenol, mixture of chloroform and isoamyl alcohol with a volume ratio of 24:1, sodium acetate, anhydrous ethanol, 70% ethanol and TE solution, % herein refer to as volume percentages, more preferably a DNA Extraction Kit manufactured by Qiagen.

The DNA polymerase is conventional in the art, preferably KOD-Plus DNA polymerase manufactured by TOYOBO.

The dNTP is conventional in the art, preferably a mixture of dATP, dGTP, dCTP and dTTP.

The Buffer is a buffer system compatible with the DNA polymerase, preferably a KOD-Plus DNA polymerase buffer manufactured by TOYOBO.

The instruction describes the use method of the kit, and preferably description of the instruction comprises steps of
(i) extracting sample genomic DNA;
(ii) identifying PRPS1 mutant genes in sample genomic DNA obtained from step (i).

In step (ii), the method for identifying the PRPS1 mutant gene in the sample genomic DNA obtained from step (i) is conventional in the art, preferably amplifying the exons of PRPS1 using the sample genomic DNA obtained from step (i) as template, and sequencing the amplified fragments.

Preferably, the description of instruction further comprises step (iii): the sample is considered to be from a subject having a risk of drug resistance and relapse of ALL if any one or more PRPS1 mutant genes in the PRPS1 mutant genes library is detected in the sample genomic DNA. If the PRPS1 mutant gene is detected, the sample is considered to be from a subject at risk of drug resistance and relapse.

The present invention provides a detection method for evaluating the risk of drug resistance and relapse of ALL in patient, which comprises steps of
(i) extracting the sample genomic DNA;
(ii) identifying the PRPS1 mutant genes in sample genomic DNA obtained from step (i).

In step (i), the sample is conventional in the art, preferably, the sample is bone marrow-derived or peripheral blood-derived tumor cells or in vitro cultured immortalized cell lines from the patients to be tested.

In step (i), extraction of the sample genomic DNA is conventional in the art, preferably DNA extraction kit manufactured by Qiagen In step (ii), the method for identifying the PRPS1 mutant genes in the sample genomic DNA obtained from step (i) is conventional in the art, preferably, identifying the PRPS1 mutant genes by PCR amplification of the exons of PRPS1 using the sample genomic DNA obtaining from step (i) as template, and sequencing the amplified fragments. Said PCR amplification is conventional in the art, preferably, amplifying PCR products using the following conditions:

Specific PCR System:

| | |
|---|---|
| 10 × KOD Buffer | 2 μL |
| 2 mM dNTP | 2 μL |
| 25 mM MgSO$_4$: | 0.8 μL |
| Forward primer (10 pmol) | 0.5 μL |
| Reverse primer (10 pmol) | 0.5 μL |
| Genomic DNA template | 1 μL(50 ng) |
| Sterile water | 12.7 μL |
| KOD-PLUS polymerase | 0.5 μL |

Specific PCR Procedure:
95° C. for 10 min (Pre-denaturation)
95° C. for 10 sec (denaturation)
55° C. for 30 sec (annealing)
68° C. for 15 sec (elongation)
30 cycles
68° C. for 10 min.

The technology of sequencing is conventional in the art, preferably conventional sequencing or next-generation sequencing.

Preferably, the detection method further comprises step (iii): evaluating the risk of drug resistance and relapse of ALL by the following criteria: the sample is considered to be from a subject at a risk of drug resistance and relapse of ALL if any one or more PRPS1 mutant genes in the PRPS1 mutant genes set is detected in the sample genomic DNA.

In a third aspect, the present invention provides a kit for evaluating the risk of drug resistance and relapse of ALL, wherein the kit comprises instruction and reagents for identifying a PRPS1 mutant genes in the PRPS1 mutant genes library.

The reagents are conventional in the art, preferably reagents identifying enzyme activity of the PRPS1 mutant, more preferably PRPP and glucose labeled with isotopic carbon atoms.

The glucose labeled with isotopic carbon atoms is conventional in the art, preferably labeled with isotope $^{13}$C. The PRPP is conventional in the art, preferably PRPP manufactured by Sigma.

Preferably, the kit further comprising cell lysis reagents is conventional in the art, preferably 80% methanol, wherein the percentage is a volume percentage.

Preferably, the kit also comprises a glucose-free medium, the glucose-free medium is a conventional in the art, preferably glucose-free medium purchasing from Gibco.

The instruction describes guidelines for the use of the kit, and the description of the instruction preferably comprises steps of
(i) lysing sample cells;
(ii) identifying the PRPS1 mutant in the cell lysate obtained from step (i).
wherein the lysing of sample cells in step (i) is conventional in the art. The detection of the PRPS1 mutant in the cell lysate obtained from step (i), which is described at step (ii), is conventional in the art, preferably detceting enzyme activity of PRPS1. Preferably, the contents of the instruction further comprises step (iii), the sample is considered to be having a risk of drug resistance and relapse of ALL if any PRPS1 mutant having a higher enzyme activity compared with that of wild type has been identified. The PRPS1 mutant is preferably any one or more mutants selected from the PRPS1 mutant library described in the second aspect of the present invention.

The present invention provides a method for evaluating the risk of drug resistance and relapse of childhood ALL by detecting PRPS1 enzyme activity, wherein said method comprises steps of
(i) lysing sample cells;
(ii) identifying the PRPS1 mutant in the cell lysates obtained from step (i).

Preferably, the method comprises steps of
(a) isolating leukemia cells from ALL patients;
(b) culturing the leukemia cells as set forth in step (a);
(c) treating the leukemia cells as set forth in step (b) using a chemotherapeutic drug;
(d) collecting and lysing the leukemia cells as set forth in step (c);
(e) identifying PRPP contents using LC-MS.

The chemotherapeutic drug in step (c) is conventional in the art, preferably purine analogues, more preferably 6-MP or 6-TG.

Lysing in step (d) is conventional in the art, preferably lysing the leukemia cells using 80% methanol.

The identification in step (e) is conventional in the art, preferably identifying the content of PRPP using LC-MS technology.

In a forth aspect, present invention provides a method for detecting drugs activity on treating and preventing drug resistance and relapse of childhood ALL, wherein the method comprises steps of
(i) contacting the compound with leukemia cells comprising any of the PRPS1 mutant genes in the PRPS1 mutant genes liabrary and harvesting pretreated leukemic cells;
(ii) contacting anti-leukemia chemotherapeutic drug with the pre-treated leukemia cells obtained from step (i).

The method preferably further comprises step (iii), wherein step (iii) comprises identifying survival rate of cells obtained from step (ii).

The present invention provides a method of screening drugs for treating and preventing drug resistance and relapse of children ALL, where the method comprises steps of
(i) contacting the candidate compound with leukemia cells comprising any of the PRPS1 mutant genes in the PRPS1 mutant genes and harvesting pretreated leukemic cells;
(ii) contacting anti-leukemia chemotherapeutic drug with the pre-treated leukemia cells obtained from step (i).

In this invention, the leukemia cells expressing the PRPS1 mutant gene in step (i) are conventional in the art, preferably human cells, more preferably human lymphocytes, most preferably Reh cells or Jurkat cells. The candidate compounds are conventional in the art, preferably conventional compounds, natural products or nucleic acids, more preferably compounds, natural products or nucleic acids targeting the purine synthesis pathway; wherein the candidate compound is of potentially reversing effect on drug resistance and relapse of ALL.

Said contacting is conventional in the art, preferably the candidate compound is capable of directly contacting with the leukemic cells, more preferably adding the candidate compound to the culture medium of the leukemic cells directly.

As used herein, said treating is conventional in the art in step (ii), preferably the chemotherapeutic drug is capable of directly contacting with the leukemic cells, more preferably adding the chemotherapeutic drug to the culture medium of the leukemic cells directly. The chemotherapeutic drug is preferably purines drugs, wherein the purines drugs is preferably 6-MP or 6-TG.

Preferably, as a control, the candidate compound is not contacted with leukemia cells comprising any of the PRPS1 mutant genes in the PRPS1 mutant library in step (i).

Preferably, the method further includes step (iii) which is identifying the survival rate of the cells obtained from step (ii). The identifying method of step (iii) is conventional in the art, preferably using a counting method after staining with viable cells, a MTT method or a method for measuring the intensity of emitted fluorescence after binding luciferase to ATP in survival cells, more preferably commercially available detection kits, such as Cell Titer-Glo reagent manufactured by Promega.

Preferably, step (iii) identifying cell's survival rate of control at step (ii) synchronously. Drug to-be-tested is of reversing effect on drug resistance and relapse of ALL when compared the survival rates and the survival rate of the sample cells is significantly lower than that of the control cells.

As used herein, said resistance and relapse refers to the patient suffering from ALL becomes tolerant to the treatment of the chemotherapeutic drug during convalescence. The chemotherapeutic drug is conventional in the art, preferably chemotherapeutic purines drugs, more preferably 6-MP or 6-TG.

Said prevention refers to an action for preventing or reducing the occurrence of said drug resistance and relapse in the case of possible drug resistance and relapse.

Said treatment refers to reducing the severity of drug resistance and relapse or curing the drug resistance and relapse of the ALL patients to make them returned to normal or slowing down the progression of the drug resistance and relapse.

In a fifth aspect, the present invention provides a drug target for preventing and treating drug resistance and relapse of ALL, wherein the target is one or more enzymes in the purine de novo synthesis pathway.

In the present invention, the target is preferably one or more targets selected from PRPS1, PRPS2, PPAT, PFAS, GART, ATIC, PAICS and ADSL.

In a sixth aspect, the present invention provides a siRNA comprising a sense RNA fragment and an antisense RNA fragment, wherein the sense RNA fragment comprises an RNA molecule encoding by the DNA of the target of claim 1, and the sense RNA fragment and the antisense RNA fragment can complement each other to form double-stranded RNA molecules.

In a seventh aspect, the present invention provides a guide RNA targeting to the GART gene, wherein the nucleotide sequence of guide RNA is shown in SEQ. ID No. 41.

In an eighth aspect, the present invention provides a lentiviral vector, wherein the lentiviral vector comprises DNA sequence of said guide RNA in the seventh aspect of the present invention and the Cas9 gene.

As used herein, the empty load of the lentiviral vector is conventional in the art, preferably lentiviral vector based on HIV-1, more preferably, lentiCRISPR purchased from Addgene.

In a ninth aspect, the present invention provides a lentivirus, wherein the lentivirus is formed by packaging the lentiviral vector as described in the eighth aspect into a virus with the aid of a lentiviral packaging plasmid in a cell line.

As used herein, the lentiviral packaging plasmid is conventional in the art, preferably psPAX2 and pMD2.g. The cell line is conventional in the art, preferably HEK293T cell line.

As used herein, said virus packaging is conventional in the art and preferably packaged virus is obtained by co-transfecting the lentiviral vector comprising down-regulated GART gene and the lentiviral packaging plasmid into the cell line, and then culturing the cell line, collecting and concentrating the supernatant from culture medium. The concentrating is conventional in the art, preferably using Amicon Ultra-15 100 KD ultrafiltration tube (Millipore) s to centrifuge and concentrate the collected virus solution at 4° C. for 30 minutes.

In a tenth aspect, the present invention provides a guide RNA targeting to the ATIC gene, wherein the nucleotide sequence of guide RNA is shown in SEQ. ID No. 42.

In a eleventh aspect, the present invention provides a lentiviral vector, wherein the lentiviral vector comprises the DNA sequence of the guide RNA as described in the tenth aspect of the present invention and the Cas9 gene.

As used herein, the empty load of the lentiviral vector is conventional in the art, preferably lentiviral vector based on HIV-1, more preferably lentiCRISPR purchased from addgene.

In a twelfth aspect, the present invention provides a lentivirus, wherein the lentivirus is formed by packaging the lentiviral vector as described in the eleventh aspect into a virus with the aid of a lentiviral packaging plasmid in a cell line.

As used herein, the lentiviral packaging plasmid is conventional in the art, preferably psPAX2 and pMD2.g. The cell line is conventional in the art, preferably HEK293T cell line.

As used herein, the virus packaging is conventional in the art and preferably, packaged virus is obtained by co-transfecting the lentiviral vector comprising down-regulated ATIC gene and the lentiviral packaging plasmid into the cell line, and then culturing the cell line, collecting and concentrating the supernatant from culture medium. The concentrating is conventional in the art, preferably using Amicon Ultra-15 100 KD ultrafiltration tube (Millipore) to centrifuge and concentrate the collected virus solution at 4° C. for 30 minutes. In the eighth and eleventh aspect of the present invention, Cas9 gene of the lentiviral vector is conventional in the art, preferably a Cas9 gene optimized according to the human genetic codon.

In a thirteenth aspect, the present invention provides a use of the guide RNA according to the seventh and/or tenth aspect, the lentiviral vector according to the eighth and/or eleventh aspect, or the lentiviral according to the ninth or twelfth aspect in preparation of drugs for preventing or treating drug resistance and relapse of ALL.

In a fourteenth aspect, the present invention provides a pharmaceutical composition for preventing and treating drug resistance and relapse of ALL, wherein the effective substance comprises one or more components selected from the siRNA as set forth in the sixth aspect, the guide RNA as set forth in the seventh and/or tenth aspect, the lentiviral vector set forth in the eighth and/or eleventh aspect and the lentiviral as set forth in the ninth and/or twelfth aspect of the present invention.

In a fifteenth aspect, the present invention provides a use of inhibitors of one or more enzymes in the purine de novo synthesis pathway in preparing drugs for preventing or treating drug resistance and relapse of ALL.

As used herein, the inhibitor is conventional in the art, preferably one or more inhibitors selected from inhibitory RNA, inhibitory polypeptides, antibodies and small molecule compound inhibitors, more preferably one or more inhibitors selected from inhibitory RNA and small molecule compounds inhibitors. The inhibitory RNA is conventional in the art, preferably one or more RNAs selected from guide RNA, siRNA, shRNA, miRNA, antisense RNA and ribozyme, more preferably one or more RNAs selected from guide RNA, siRNA and shRNA, most preferably guide RNA, where in the sequence of guide RNA is shown in SEQ ID NO. 41 or SEQ ID NO. 42. The small molecule compound inhibitor is conventional in the art, preferably one or two inhibitors selected from Lometrexol and Alimta, more preferably Lometrexol.

As used herein, said resistance and relapse refers to the patient suffering from ALL becomes tolerant to the treatment of the chemotherapeutic drug during convalescence. The chemotherapeutic drug is preferably chemotherapeutic purines drugs, more preferably 6-MP or 6-TG.

Said prevention refers to an action for preventing or reducing the occurrence of said drug resistance and relapse in the case of possible drug resistance and relapse.

Said treatment refers to reducing the severity of drug resistance and relapse or curing the drug resistance and relapse of the ALL patients to make them returned to normal or slowing down the progression of the drug resistance and relapse.

The drugs for preventing or treating drug resistance and relapse of ALL comprises one or more of inhibitory RNA, the inhibitory polypeptide, an antibody and a small molecule compound inhibitor, and a pharmaceutical carrier. In said drugs, one or more of inhibitory RNA, the inhibitory polypeptide, the antibody and the small molecule compound inhibitor can be used alone or in combination with other components as an active ingredient. The active ingredient refers to having the function of preventing and treating drug resistance and relapse. The pharmaceutical carriers include pharmaceutically acceptable excipients, fillers, diluents, and the like.

In said drugs, the content of one or more of RNA, the inhibitory polypeptide, the antibody and the small molecule compound inhibitor is 0.01 to 99.99%, and the content of the pharmaceutical carrier is 0.01 to 99.99%, wherein the percentage is the mass percentage of the total mass of the drug.

The form of the drug is not-restricted herein and can be solid, semi-solid or liquid, can be an aqueous solution, a non-aqueous solution or a suspension, or a tablet, a capsule, a granule, an injection or an infusion. The drugs can be administered orally, or administered by intravenous, intramuscular, intradermal or subcutaneous injection.

As used herein, the dosage of the drug for preventing or treating the drug resistance and relapse of ALL is determined depending on the age and condition of the patient, and the usual daily dose is about 0.0001 to 1000 mg/kg, preferably 0.01 to 500 mg/kg, more preferably 0.1 to 200 mg/kg body weight. The administration frequency is once or several times a day.

As used herein, the drug for preventing or treating the drug resistance and relapse of ALL may also be used in combination with a chemotherapeutic drug during treatment. The chemotherapeutic drugs are conventional in the art, preferably purine chemotherapy drugs, more preferably 6-mercaptopurine (6-MP) or 6-mercaptopurine (6-TG).

In a sixteenth aspect, the present invention provides a kit for evaluating the risk of drug resistance and relapse of ALL, wherein it comprises reagents for lysing sample cells and identifying one or more of hypoxanthine (HX), hypoxanthine nucleotide monophosphate (IMP), 5-aminoimidazole-4-carboxamide nucleotides (AICAR) and Inosine, and an instruction, wherein the instruction describes contents including steps of
(a) collecting and lysing the sample cells;
(b) identifying the contents of one or more of HX, IMP, AICAR and Inosine in the sample cell lysate obtained from step (a);
(c) evaluating the risk of drug resistance and relapse of ALL by determining the concentration of one or more substances of HX, IMP, AICAR and Inosine obtained from step (b).

As used herein, the kit preferably further comprises a standard sample, wherein the standard sample is conventional in the art, preferably one or more of HX, AICAR and Inosine, more preferably one or more of AICAR, Inosine and HX, wherein all carbon atoms are $^{13}C$, and all nitrogen atoms are $^{15}N$ in HX.

As used herein, the reagent for lysing cell is conventional in the art, preferably 80% methanol, wherein the percentage is a volume percentage.

As used herein, the reagents for identification of one or more of HX, IMP, AICAR and Inosine is conventional in the art, preferably mass spectrometry reagents.

The present invention also provides a method for evaluating the risk of drug resistance and relapse of ALL, wherein the method includes steps of
(a) collecting and lysing the sample cells;
(b) identifying the contents of one or more of HX, IMP, AICAR and Inosine in the sample cell lysate obtained from step (a);
(c) evaluating the drug resistance and relapse of ALL by determining the concentration of one or more of HX, IMP, AICAR and Inosine obtained from step (b).

In this method, the sample cells in step (a) is conventional sample cells of ALL in the art, preferably sample cells of ALL containing the PRPS1 mutants as described above, more preferably Reh cells containing the PRPS1 mutants, most preferably Reh-PRPS1-S103T cells or Reh-PRPS1-A190T cells. Said lysing is conventional in the art, preferably 80% methanol, and the percentage is a volume percentage. In step (b), said identifying can be conventional identification method, preferably mass spectrometric identification.

The preferred embodiments of the present invention can be arbitrarily combined on the basis of common knowledge in the art.

The reagents and materials used in the present invention are commercially available.

The positive effect of the invention is that, the present invention provides a mutant gene related to drug resistance and relapse of ALL, which is a new target for treating drug resistance and relapse of ALL, to address the existing problem that using nucleoside analogues as a chemotherapeutic drug to treat ALL will lead to drug resistance and relapse. A risk assessment of childhood ALL can be achieved by the kit for evaluating the risk of the drug resistance and relapse of ALL based on the mutant genes. In addition, the present invention provides a use of a novel drug targeting on enzymes in purine synthesis pathway in prevention and treatment of ALL to address the existing problem that using nucleoside analogues as a chemotherapeutic drug in the treatment of ALL will lead to drug resistance and relapse. The present invention also provides a novel kit for evaluating the risk of drug resistance and relapse of ALL wherein the kit evaluates one or more of metabolites selected from hypoxanthine nucleotide, HX, AICAR and Inosine in purine synthesis pathway as one of the indicators to assess the risk of drug resistance and relapse of ALL, and provides a strong technical means and support for the prevention and treatment of drug resistance and relapse of ALL.

BRIEF DESCRIPTION OF THE DRAWINGS

FIG. 1A: Schematic diagram showing relapse-specific PRPS1 missense mutations and affected protein domains. FIG. 1B: Emergence of relapse-specific PRPS1 mutations during remission, as detected by ultra-deep sequencing (mean, 250,000 reads). Key indicates sample ID of specific study individuals and their respective PRPS1 mutations.

FIG. 7A: Viability of stable Reh cell line treated by different concentration of 6-MP. FIG. 7B: Viability of Reh cell line treated by different concentration of 6-TG. FIG. 7C: $IC_{50}$ of 6-MP and 6-TG of the cell lines expressing PRPS1 wild-type and mutants.

FIG. 8A: Apoptosis of cells expressing WT PRPS1 or drug-resistant mutants after treatment for 72 h with 10 μg/ml 6-MP or 6-TG. FIG. 8B: DNA damage response and apoptosis biomarkers in a western blot analysis of Reh cells with the indicated PRPS1 mutations and treated with 10 μg/ml 6-MP.

FIG. 9A: Intracellular concentration of TIMP, TGMP, r-MP, r-TG and r-MMP (in an order from upper left to lower right, respectively), as measured by LC-MS, within Reh cells expressing various PRPS1 mutants and treated with 10 μM 6-MP for 4 h. Values are relative concentrations estimated on the basis of standard curves of pure compounds without correcting for the cell matrix's effect. FIG. 9B: Heat map showed metabolomics analysis of nucleotides, de novo purine flux, purine salvage flux and PRPS1 activity in Reh cells expressing different PRPS1 variants. FIG. 9C: Diagram illustrating incorporation of $[^{13}C2, ^{15}N]$-glycine into the de novo purine biosynthesis pathway, $[^{13}C_5, ^{15}N_4]$-HX into the purine salvage pathway, and $[^{13}C_6]$-glucose into PRPP, which leads to both de novo and salvage pathways.

FIG. 10A: Diagram illustrating incorporation of $[^{13}C2, ^{15}N]$-glycine into the de novo purine biosynthesis pathway, $[^{13}C_5, ^{15}N_4]$-HX into the purine salvage pathway, and $[^{13}C_6]$-glucose into PRPP, which leads to both de novo and salvage pathways.

FIG. 10B: Comparison of the concentration of PRPP product catalyzed by the control group and each PRPS1 mutant gene in the experimental group.

FIG. 12A: Feedback inhibition of WT and mutant PRPS1 enzyme activities by GDP, showing titration curves for WT PRPS1, two representative drug-resistant mutants and one reduced-function mutant. FIG. 12B: Inhibition of GDP/ADP on protein activity of PRPS1 WT, representative drug-resistant mutants and reduced-function mutants. FIG. 12C: Nucleotide feedback inhibition of PRPS1 activity measured by $[^{13}C_5]$-PRPP in cells expressing WT PRPS1 and representative drug-resistant mutants.

FIG. 13A: Reductive concentrations of IMP in Reh cells expressing PRPS1 WT and drug resistance mutations. FIG. 13B: Reductive concentrations of hypoxanthine in Reh cells expressing PRPS1 WT and drug resistance mutations. FIG. 13C: Reductive concentrations of AICAR in Reh cells expressing PRPS1 WT and drug resistance mutations. FIG. 13D: Reductive concentrations of Inosine in Reh cells expressing PRPS1 WT and drug resistance mutations. FIG. 13E: Reductive concentrations of IMP+9 in Reh cells expressing PRPS1 WT and drug resistance mutations.

FIG. 14A: The impact of GART and ATIC on 6-MP $IC_{50}$ (left) and hypoxanthine cell concentration (right) of WT and mutants. FIG. 14B: Protein electrophoresis map indicated the impact of inhibitory effect of CRISPR guide RNA targeting purine synthesis pathway on the drug resistance of PRPS1 S103T and A190T mutants.

FIG. 15A: Viability of Reh cells at increasing concentrations of 6-MP and in the presence of HX. FIG. 15B: Viability of Reh cells at increasing concentrations of 6-MP and in the presence of IMP.

FIG. 16A: Relative concentration of TIMP. FIG. 16B: Relative concentration of TGMP.

FIG. 17A: The establishment of in vitro enzymatic reaction. FIG. 17B: Left, HX is preferred to 6-MP as an HPRT1 substrate. LC-MS measured the concentrations of reaction products (IMP, TIMP), Right, HX can suppress 6-MP prodrug conversion. Increasing concentrations of HX were added to compete the 6-MP conversion, and the TIMP concentration was measured by LC-MS.

FIG. 18A: $IC_{50}$ of 6-MP on Reh cells with or without 5 ng/ml lometrexol. FIG. 18B: Hypoxanthine concentration of Reh cells with or without 5 ng/ml lometrexol. FIG. 18C: Relative TIMP concentration of cells treating with or without lometrexol. FIG. 18D: Relative TGMP concentration of cells treating with or without lometrexol.

FIG. 19A: PRPS1 expression in Reh cells were knocked down using Lentiviral shRNAs. FIG. 19B: Relative expression level of PPAT RNA. FIG. 19C: $IC_{50}$ of 6-MP shows the inhibitory effect of nucleic acid drug shRNA.

DETAILED DESCRIPTION OF THE PREFERRED EMBODIMENT

The invention is further illustrated by means of embodiments, but the invention is not limited to the scope of the described embodiments. The experimental methods without specified conditions in the following embodiments are selected according to conventional methods and conditions, or in accordance with the product instruction.

Figure 1:
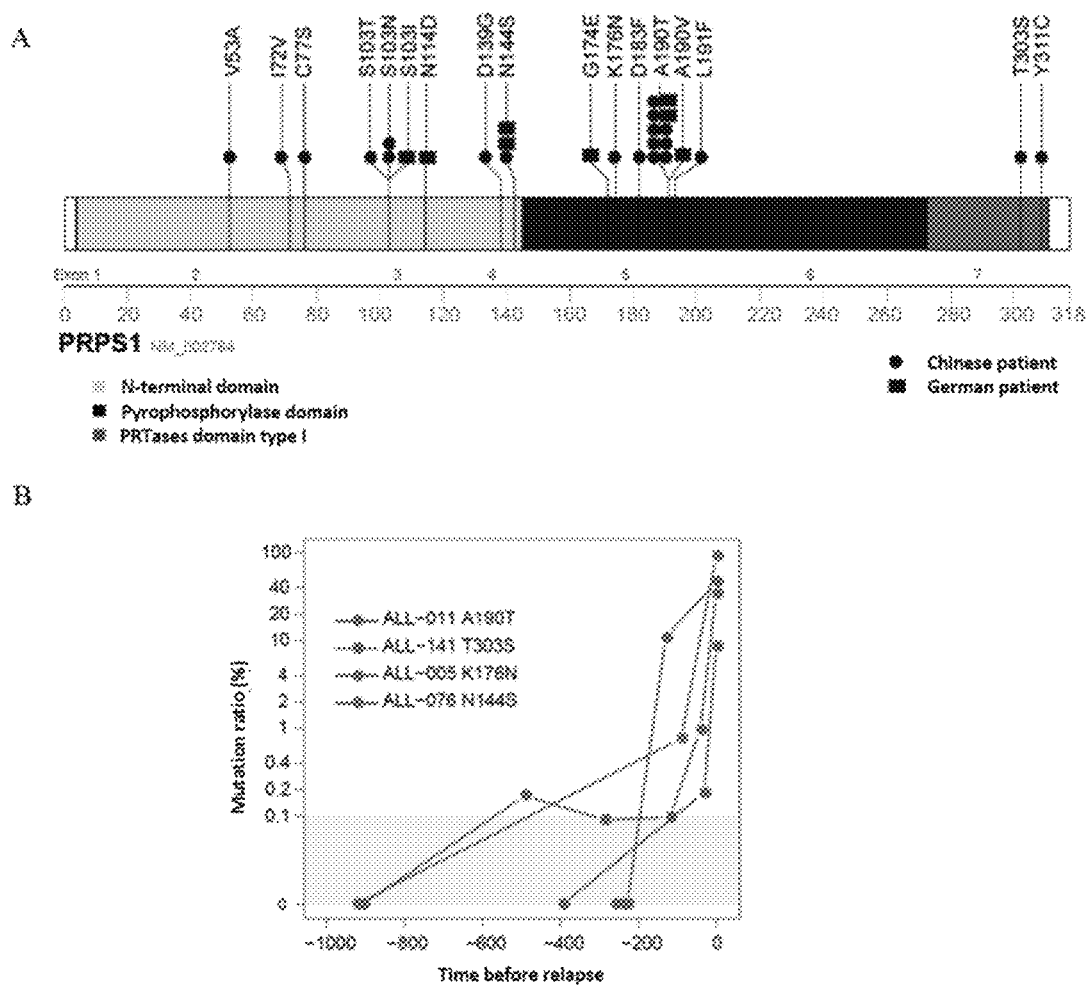
FIG. 1 PRPS1 was found to be mutated relapse-specifically using super-deep sequencing and the mutation rate was found to be increased rapidly before clinical relapse.

As used herein, the samples from 16 groups of childhood ALL in the phase of diagnosis, remission and relapse were sequenced by Whole Exome Sequencing technology, and it was found that the phosphoribosyl pyrophosphate synthase I gene has relapse-specific multiple sites mutations, and the genes in diagnosis and remission samples remain wild type genes. In the further sequencing of PRPS1 gene in 144 relapsed samples, PRPS1 gene mutation was found in 16 relapsed samples, and the mutation frequency was 13% (18/138) in B-ALL. In the meantime, Dr. Renate Kirschner-Schwarb from the Pediatric Blood and Cancer Center of Charité—Universitätsmedizin Berlin in Germany also confirmed that there was a relapse-specific mutation in PRPS1 in German Childhood ALL with a mutation rate of 2.7% (6/220). None of the most important four types of mutations A190T, T303S, K176N and N144S in all mutations have been found in all samples from ALL patients within the resolution range by ultra-deep sequencing a series of bone marrow samples during the diagnosis. In addition, these PRPS1 mutations were found to grown exponentially before the clinical phase of relapse, as shown in FIG. 1. After overexpressing the PRPS1 mutant gene in ALL cell line Reh which usually expressed wild-type PRPS1, it was shown that the relapse-specific PRPS1 gene mutations resulted in a resistance of Reh to 6-MP/6-TG in drug susceptibility test, which demonstrates that PRPS1 gene mutation plays an important role in the progress of drug resistance and relapse of childhood ALL.

In combination with the methods of cell biology, molecular biology, metabonomics and the like, the present invention systematically studied the mechanism of drug resistance and relapse of childhood ALL which is regulated by PRPS1 gene mutation, from the aspects of the effect of PRPS1 gene mutation on its own enzyme activity, to its effect on the metabolism network of 6-MP drug and purine. The study revealed a new mechanism of drug resistance and relapse of Childhood ALL, suggesting that PRPS1 mutations can drive relapse and be the marker of drug resistance and relapse, meanwhile PRPS1 mutations have important implications for subsequent gene diagnosis and individualized treatment in early phase of clinical relapse.

Figure 2:
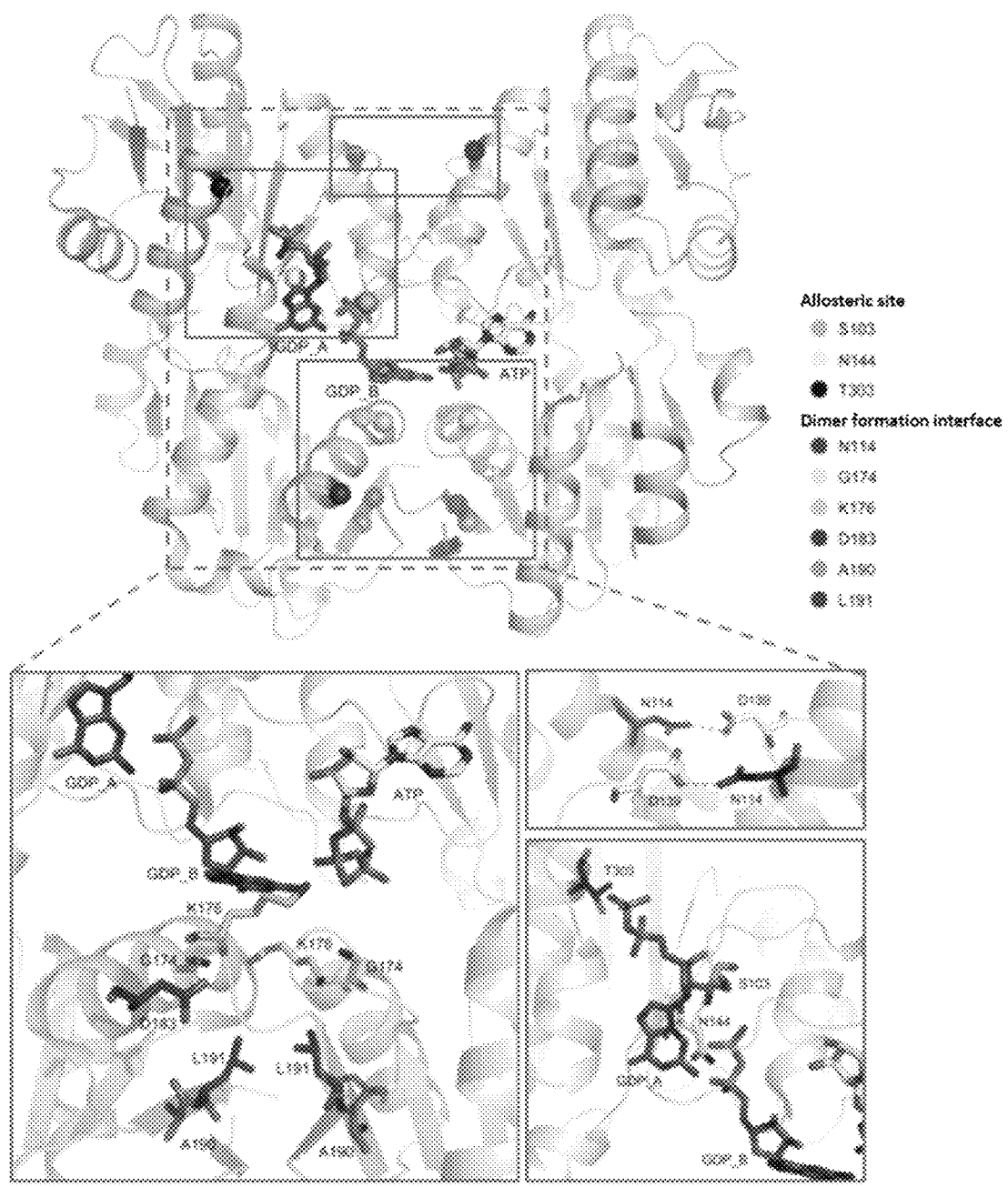
FIG. 2 Structural representation of PRPS1 mutant protein.

In the following embodiments, the D183H mutant, as gain-of-function mutant of the reported PRPS1 gene, and A87T and M115T mutants, as loss-of functions mutant of the reported PRPS1 gene, are used as the positive control and negative control, respectively, to evaluate whether the system of experimental detection is normal. As for the experimental groups, the mutants of S103T, S103N, N144S, T303S, K176N, D183E, A190T, A190V, A190V and L191F can be divided into two groups by comparing their crystal structure with that of human PRPS1, namely mutants having the mutation sites located at the dimer formation interface of PRPS1 and mutants having the mutation sites located at allosteric sites of PRPS1, which were shown in FIG. 2. The mutants within the group are drug-resistant mutants of the PRPS1 gene.

Embodiment 1

Identification of PRPS1 Gene Mutations in Samples:
PRPS1 sequencing was performed in 16 group of diagnostic, remission and relapse samples from subjects having childhood ALL and 144 relapsed samples using Whole Exome Sequencing technology.

Quality control of the samples: The quality of the samples is directly related to the reliability of the sequencing results. The quality of the samples used for deep sequencing and subsequently validation is guaranteed by the following three methods: (i) In the stage of diagnosis and relapse, leukemia cells in the bone marrow may account for more than 90% of the nucleated cells, and residual normal granulocytes and nucleated red blood cells can be removed by Ficoll density gradient centrifugation to obtain leukemia cells with high purity used for subsequently DNA extraction and sequencing; (ii) Leukemia cells and normal bone marrow hematopoietic cells can be differentiated by multicolor fluorescent antibody combination, and samples with low purity can be sorted by flow cytometry to obtain samples with high purity (>99%); (iii) According to trace residual in the test results, samples in remission stage with the residual leukemia cells below 0.01% were selected for deep sequencing, thus ensuring the reliability of mutations specifically in the stage of diagnosis and relapse.

Preparation of the samples: Genomic DNA from leukemia cells was extracted using QIAGEN Blood DNA kit, DNA concentration was determined using Q-bit Fluorescence Quantification Kit, and high purity of genomic DNA was used for subsequent deep sequencing.

Amplification of PRPS1 exons: Amplification of PRPS1 exons was implemented by using suitable primers designed for genome sequence of PRPS1, wherein the PCR system and program are as follows:

Specific PCR System:

| | |
|---|---|
| 10 × KOD Buffer | 2 μL |
| 2 mM dNTP | 2 μL |
| 25 mM MgSO$_4$: | 0.8 μL |
| Forward primer (10 pmol) | 0.5 μL |
| Reverse primer (10 pmol) | 0.5 μL |
| Genomic DNA template | 1 μL(50 ng) |
| Sterile water | 12.7 μL |
| KOD-PLUS polymerase | 0.5 μL |

Specific PCR Program:
95° C. for 10 min (Pre-denaturation)
95° C. for 10 sec (denaturation)
55° C. for 30 sec (annealing)
68° C. for 15 sec (elongation)
68° C. for 10 min.

Primer sequences are shown in Table 1. PCR products were routinely subjected to capillary electrophoresis sequencing and mutation analysis, and mutation analysis was performed using the software Mutation Surveyor.

Sequencing analysis: The target bands were sequenced after PCR successfully. The target sequence was compared with the PRPS1 gene sequence in NCBI to analyze the gene mutation of PRPS1. The experimental results are shown in Table 2 and Table 3.

By sequencing the diagnostic, remission and relapse samples of 16 groups of children with ALL, it was found that there were multiple relapse-specific mutations in the PRPS1 (phosphoribosyl pyrophosphate synthase I) gene (see Table 2), while the PRPS1 is wild-type in diagnostic and remission samples. PRPS1 sequencing was conducted in 144 relapse samples and PRPS1 gene mutation was found in 16 relapse samples with a mutation frequency of 13% (18/138). In the meantime, Dr. Renate Kirschner-Schwarb in the Pediatric Blood and Cancer Center of Charité-Universitätsmedizin Berlin in Germany also confirmed the results of this invention and there was a relapse-specific mutation in PRPS1 in German Childhood ALL with a mutation rate of 2.7% (6/220) (see Table 2). Combined with clinical pathology analysis, it was shown that patients with PRPS1 mutations were in the early stage of relapse (P<0.005) (see Table 3). By ultra-deep sequencing, it was found that PRPS1 was a relapse-specific mutation and the mutation ratio increased rapidly before clinical relapse which means PRPS1 drives the relapse of patient and can be used as a genetic marker for clinical relapse diagnosis and an important target for therapy of clinical relapse.

TABLE 1

Information of PCR for amplifying exons

| PRPS exons | Primer sequence (5'-3') | Annealing Temperature |
|---|---|---|
| Exon 1 | Forward: TGAGTCTGTGGCCGACTTC (SEQ ID NO: 3) Reverse: CGACCCCATCCCTCCTATAC (SEQ ID NO: 4) | 63° C. |
| Exon 2 | Forward: TCAATCCACACTTGGTTGAATC (SEQ ID NO: 5) Reverse: TCCAGAGGAGTTGGTGCTTAG (SEQ ID NO: 6) | 63° C. |
| Exon 3 | Forward: ATGAATTTCTGGGTACCATAGTG (SEQ ID NO: 7) Reverse: CTTCTCTGCAGTCTTCAGCATC (SEQ ID NO: 8) | 63° C. |
| Exon 4 | Forward: AATCTACCACACTGGGCCTG (SEQ ID NO: 9) Reverse: CCATGTGCTAGCTACTTACATCC (SEQ ID NO: 10) | 63° C. |
| Exon 5 | Forward: CCCCGGCCTCTTTAGTCC (SEQ ID NO: 11) Reverse: TCAGCAGGCTGAAGACATTC (SEQ ID NO: 12) | 58° C. |
| Exon 6 | Forward: GTTGTGGAAGCCTAAGCAGG (SEQ ID NO: 13) Reverse CTTCAGAATCCAGAGACCTAATTC (SEQ ID NO: 14) | 63° C. |
| Exon 7 | Forward: TCATGACAGGGAAACAGCAC (SEQ ID NO: 15) Reverse: GAGCTTCCCCAGTCACAGTC (SEQ ID NO: 16) | 63° C. |

TABLE 2

PRPS1 mutations in relapse samples of Chinese and German childhood B-ALL

|  | Sample ID | Immuno-phenotype | Site on chromosome | Base transformation | Amino acids transformation | Case Amount | Mutation frequency (%) |
|---|---|---|---|---|---|---|---|
| China | ALL-122 | B | ChrX: 106,882,560 | T > C | V53A | 1 | 13.0 (18/138) |
|  | ALL-102 | B | ChrX: 106,882,616 | A > G | I72V | 1 |  |
|  | ALL-157 | B | ChrX: 106,882,632 | G > C | C77S | 1 |  |
|  | ALL-058 | B | ChrX: 106,884,133 | G > C | S103T | 1 |  |
|  | ALL-088 | B | ChrX: 106,884,133 | G > A | S103N | 2 |  |
|  | ALL-151 | B | ChrX: 106,884,133 | G > A | S103N |  |  |
|  | ALL-128 | B | ChrX: 106,885,606 | A > G | D139G | 1 |  |
|  | ALL-076 | B | ChrX: 106,885,621 | A > G | N144S | 1 |  |
|  | ALL-005 | B | ChrX: 106,885,718 | G > C | K176N | 1 |  |
|  | ALL-005 | B | ChrX: 106,888,425 | C > G | D183E | 1 |  |
|  | ALL-011 | B | ChrX: 106,888,444 | G > A | A190T | 8 |  |
|  | ALL-121 | B | ChrX: 106,888,444 | G > A | A190T |  |  |
|  | ALL-122 | B | ChrX: 106,888,444 | G > A | A190T |  |  |
|  | ALL-145 | B | ChrX: 106,888,444 | G > A | A190T |  |  |
|  | ALL-146 | B | ChrX: 106,888,444 | G > A | A190T |  |  |
|  | ALL-128 | B | ChrX: 106,888,444 | G > A | A190T |  |  |
|  | ALL-137 | B | ChrX: 106,888,444 | G > A | A190T |  |  |
|  | ALL-143 | B | ChrX: 106,888,444 | G > A | A190T |  |  |
|  | ALL-148 | B | ChrX: 106,888,449 | G > C | L191F | 1 |  |
|  | ALL-141 | B | ChrX: 106,893,213 | C > G | T303S | 1 |  |
|  | ALL-026 | B | ChrX: 106,893,237 | A > G | Y311C | 1 |  |
| German | ALL-374 | B | ChrX: 106,884,133 | G > T | S103I | 1 | 2.7 (6/220) |
|  | ALL-386 | B | ChrX: 106,884,165 | A > G | N114D | 1 |  |
|  | ALL-335 | B | ChrX: 106,885,621 | A > G | N144S | 2 |  |
|  | ALL-381 | B | ChrX: 106,885,621 | A > G | N144S |  |  |
|  | ALL-335 | B | ChrX: 106,885,711 | G > A | G174E | 1 |  |
|  | ALL-248 | B | ChrX: 106,888,445 | C > T | A190V | 1 |  |
|  | ALL-253 | B | ChrX: 106,888,444 | G > A | A190T | 2 |  |
|  | ALL-374 | B | ChrX: 106,888,444 | G > A | A190T |  |  |

In the present invention, the bone marrow samples from diagnostic, remission and relapse of children ALL were sequenced using Whole Exome Sequencing technology and PRPS1 gene mutations was found in 18 relapse samples with a mutation frequency of 13% (18/138) as shown in Table 2, wherein the A190T site mutation occurred in 9 relapse samples. The collaboration with Dr. Renate Kirschner-Schwarb in the Children's Blood Cancer Center of Charité-Universitätsmedizin Berlin in Germany also confirmed that there was a relapse-specific mutation in PRPS1 in German Children ALL with a mutation rate of 2.7% (6/220).

TABLE 3

Correlation between PRPS1 mutation and clinical features in Chinese and German children with B-ALL

|  | China (n = 138) | | | Germany (n = 220) | | |
|---|---|---|---|---|---|---|
|  | PRPS1 Wild-type (%) n = 120 | PRPS1 Mutant (%) n = 18 | P | PRPS1 Wild-type (%) n = 214 | PRPS1 Mutant (%) n = 6 | P |
| Age |  |  | 0.365[1] |  |  | 0.276[1] |
| <1 year old | 6 (5.0) | 0 (0.0) |  | 5 (2.3) | 0 (0.0) |  |
| 1-9 years old | 90 (75.0) | 12 (66.7) |  | 158 (73.8) | 3 (50.0) |  |
| >10 years old | 24 (20.0) | 6 (33.3) |  | 51 (23.8) | 3 (50.0) |  |
| Gender |  |  | 0.300[2] |  |  | 0.684[1] |
| Girl | 43 (35.8) | 9 (50.0) |  | 104 (48.6) | 2 (33.3) |  |
| Boy | 77 (64.2) | 9 (50.0) |  | 110 (51.4) | 4 (66.7) |  |
| Amount of leukocytes (×10$^9$/L) |  |  | 0.101[1] |  |  | 0.441[1] |
| <50 | 91 (75.8) | 10 (55.6) |  | 194 (91.1) | 5 (83.3) |  |
| 50-100 | 12 (10.0) | 2 (11.1) |  | 12 (5.6) | 1 (16.7) |  |
| >100 | 17 (14.2) | 6 (33.3) |  | 7 (3.3) | 0 (0.0) |  |
| No data |  |  |  | 1 | 0 |  |
| Genetic feature |  |  | 0.324[1] |  |  | 0.750[1] |
| E2A-PBX1 | 4 (4.7) | 0 (0.0) |  | 3 (1.4) | 0 (0.0) |  |
| TEL-AML1 | 9 (10.4) | 0 (0.0) |  | 34 (16.3) | 0 (0.0) |  |
| BCR-ABL1 | 17 (19.7) | 4 (44.4) |  | 4 (1.9) | 0 (0.0) |  |
| MLL-AF4 | 1 (1.2) | 0 (0.0) |  | 4 (1.9) | 0 (0.0) |  |
| Normal | 55 (64.0) | 5 (55.6) |  | 163 (78.4) | 6 (100.0) |  |
| No data | 34 | 9 |  | 6 | 0 |  |

TABLE 3-continued

Correlation between PRPS1 mutation and clinical features in Chinese and German children with B- ALL

| | China (n = 138) | | | Germany (n = 220) | | |
|---|---|---|---|---|---|---|
| | PRPS1 Wild-type (%) n = 120 | PRPS1 Mutant (%) n = 18 | P | PRPS1 Wild-type (%) n = 214 | PRPS1 Mutant (%) n = 6 | P |
| Risk degree of relapse | | | 0.203[2] | | | 0.010[1] |
| Low risk, Moderate risk | 76 (63.3) | 8 (44.4) | | 153 (71.5) | 1 (16.7) | |
| High risk | 44 (36.7) | 10 (55.6) | | 61 (28.5) | 5 (83.3) | |
| Immuno-phenotype | | | 0.456[1] | | | 1.000[1] |
| pro-B | 5 (4.9) | 0 (0.0) | | 11 (5.6) | 0 (0.0) | |
| common B | 83 (81.4) | 13 (76.5) | | 154 (78.6) | 6 (100.0) | |
| pre-B | 14 (13.7) | 4 (23.5) | | 25 (12.8) | 0 (0.0) | |
| Biphenotypic | 0 (0.0) | 0 (0.0) | | 6 (3.1) | 0 (0.0) | |
| No data | 18 | 1 | | 18 | 0 | |
| Relapse time[¶] | | | 0.002[1] | | | ≤0.001[1] |
| Relative early | 51 (42.5) | 11 (61.1) | | 28 (13.1) | 4 (66.7) | |
| Early | 26 (21.7) | 7 (38.9) | | 51 (23.8) | 2 (33.3) | |
| Late | 43 (35.8) | 0 (0.0) | | 135 (63.1) | 0 (0.0) | |
| Relapse time | | | ≤0.001[1] | | | ≤0.001[1] |
| Relapse in therapy | 77 (64.2) | 18 (100.0) | | 51 (23.8) | 6 (100.0) | |
| Relapse after therapy | 43 (35.8) | 0 (0.0) | | 163 (76.2) | 0 (0.0) | |
| NT5C2 mutation | | | | | | |
| No | 43 | 2 | | 105 (49.1) | 3 (50.0) | |
| Yes | 0 | 0 | | 7 (3.3) | 0 (0.0) | |
| No data | 77 | 16 | | 102 (47.6) | 3 (50.0) | |

[1]P value is calculated by the Fisher exact test. [2]P value is calculated by chi-square test. Relapse time[¶]: Relative early, within 18 months after diagnosis; Early, between 18 months and 36 months after diagnosis; Late, after 36 months after the initial treatment.

As shown in Table 3, after analyzing clinicopathological data, it was found that PRPS1 mutations were all occurred in patients with early relapse (Chinese patient, P<0.005, Germany patient, P<0.001), suggesting the PRPS1 mutation is significant for diagnosing relapse in remission stage.

Embodiment 2

Identification of PRPS1 Gene Mutations Involved in Purine Metabolic Pathway in Samples Sequencing of HGPRT, IMPDH, NT5C2, PRPS2, ATIC, ADSL, GART and PFAS enzymes involved in purine metabolism was performed in 160 relapse samples of childhood ALL using conventional next-generation sequencing.

Quality control and preparation of the samples, and amplification of gene exons were the same as in Embodiment 1.

Sequencing analysis: After successful PCR, the target bands were sequenced, and the target sequences were compared with the corresponding gene sequences in NCBI to analyze the gene mutation. If a mutation was found in the relapse sample, the diagnostic sample of the same patient will be detected to determine whether it is a relapse-specific mutation. The experimental results are shown in Table 4.

By sequencing and sequence alignment, it was found that there were relapse-specific mutations in purine metabolism related enzymes such as PRPS2, ATIC, ADSL, GART and PFAS.

TABLE 4

The mutations of enzymes related to purine metabolism in relapse samples of childhood ALL

| Gene name | Sample ID | Immuno-phenotype | Site on chromosome | Base transformation | Amino acids transformation | Case No. | Mutation frequency (%) |
|---|---|---|---|---|---|---|---|
| PRPS1 | ALL-122 | B | ChrX: 106,882,560 | T > C | V53A | 1 | 13 (18/138) |
| | ALL-102 | B | ChrX: 106,882,616 | A > G | I72V | 1 | |
| | ALL-157 | B | ChrX: 106,882,632 | G > C | C77S | 1 | |
| | ALL-058 | B | ChrX: 106,884,133 | G > C | S103T | 1 | |
| | ALL-088 | B | ChrX: 106,884,133 | G > A | S103N | 2 | |
| | ALL-151 | B | ChrX: 106,884,133 | G > A | S103N | | |
| | ALL-128 | B | ChrX: 106,885,606 | A > G | D139G | 1 | |
| | ALL-076 | B | ChrX: 106,885,621 | A > G | N144S | 1 | |
| | ALL-005 | B | ChrX: 106,885,718 | G > C | K176N | 1 | |
| | ALL-005 | B | ChrX: 106,888,425 | C > G | D183E | 1 | |
| | ALL-011 | B | ChrX: 106,888,444 | G > A | A190T | 8 | |
| | ALL-121 | B | ChrX: 106,888,444 | G > A | A190T | | |
| | ALL-122 | B | ChrX: 106,888,444 | G > A | A190T | | |
| | ALL-145 | B | ChrX: 106,888,444 | G > A | A190T | | |
| | ALL-146 | B | ChrX: 106,888,444 | G > A | A190T | | |
| | ALL-128 | B | ChrX: 106,888,444 | G > A | A190T | | |
| | ALL-137 | B | ChrX: 106,888,444 | G > A | A190T | | |
| | ALL-143 | B | ChrX: 106,888,444 | G > A | A190T | | |

TABLE 4-continued

The mutations of enzymes related to purine metabolism in relapse samples of childhood ALL

| Gene name | Sample ID | Immuno-phenotype | Site on chromosome | Base transformation | Amino acids transformation | Case No. | Mutation frequency (%) |
|---|---|---|---|---|---|---|---|
|  | ALL-148 | B | ChrX: 106,888,449 | G > C | L191F | 1 |  |
|  | ALL-141 | B | ChrX: 106,893,213 | C > G | T303S | 1 |  |
|  | ALL-026 | B | ChrX: 106,893,237 | A > G | Y311C | 1 |  |
| PRPS2 | ALL-114 | B | ChrX: 12,809,680 | C > A | R22S | 1 | 2.8 (3/107) |
|  | ALL-120 | B | ChrX: 12,827,354 | G > T | S106I | 1 |  |
|  | ALL-127 | T | ChrX: 12,828,244 | C > G | P173R | 1 |  |
| ATIC | ALL-140 | T | Chr2: 216,190,755 | T > C | V142A | 1 | 1.7 (2/116) |
|  | ALL-114 | B | Chr2: 216,191,545 | G > T | A178S | 1 |  |
| ADSL | ALL-060 | T | Chr22: 40,745,936 | G > A | R85Q | 1 | 0.9 (1/107) |
| GART | ALL-056 | B | Chr21: 34,876,538 | G > A | V976I | 2 | 1.9 (2/105) |
|  | ALL-077 | B | Chr21: 34,876,538 | G > A | V976I |  |  |
| PFAS | ALL-002 | B | Chr17: 8,170,084 | T > A | L945Q | 1 | 1.3 (1/81) |

Embodiment 3

Construction of Prokaryotic Expression Vector for PRPS1

1. Acquisition of the target gene fragment: primers for amplifying PRPS1 wild-type, including forward primer 5' cgcggcagccatATGCCGAATATCAAAATCTTCAG 3' (SEQ ID NO: 17), and reverse primer 5' gtggtggtgctcgagT-TATAAAGGGACATGGCTGAATAGGTA 3' (SEQ ID NO: 18), were designed according to the PRPS1 sequence provided by NCBI (gene ID: 5631, NM 002764). Primer contains exchanging-pairing base, cleavage site, and 5'end sequence of target gene used for PCR capturing target gene). Having a size of 957 bp, PRPS1 product was captured by PCR using cDNA extracted from Reh cells as template, and the product sequence was shown in SEQ ID No. 1.

Figure 3:
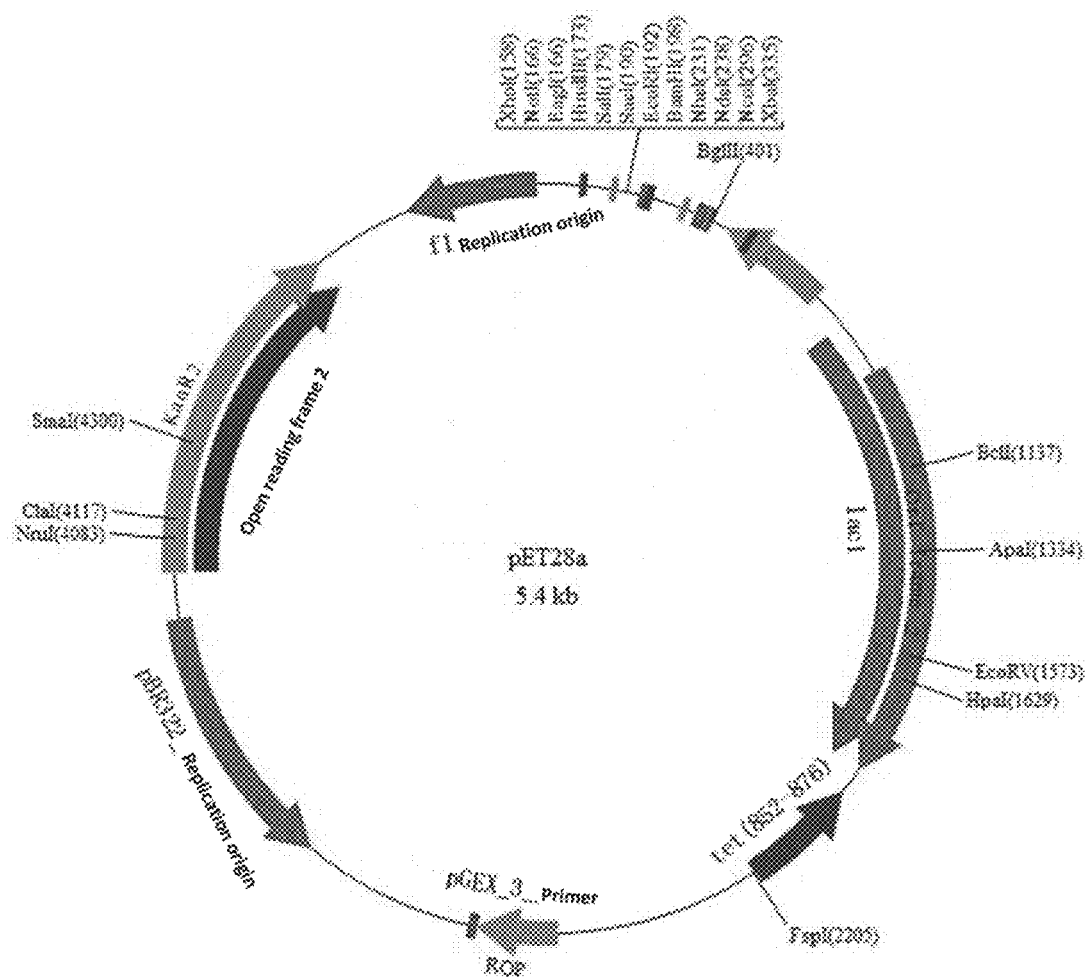
FIG. 3 Map of pET28a Vector.

2. Linearization of the prokaryotic expression vector: The pET28a vector was digested with the restriction endonuclease NdeI/XhoI, meanwhile the map of PET28a vector was shown in FIG. 3.

3. Construction of recombinant plasmid: The PCR product at Step 1 was recombinated into the linearized viral vector using In-Fusion™ PCR Cloning Kit from Clontech, and the recombinant was amplified by *E. coli* TOP10.

4. Identification of recombinant plasmids: the recombinants were confirmed by Sequencing.

5. Construction of prokaryotic vector containing PRPS1 mutant: 9 mutants of PRPS1 including S103T, S103N, N144S, T303S, K176N, D183E, A190T, A190V and L191F were constructed by circular PCR using KOD-Plus DNA polymerase with pOD28a-PRPS1 as plasmid template, wherein the PCR primers were shown in Table 5.

Specific PCR system:

| | |
|---|---|
| 10 × KOD Buffer | 2 μL |
| 2 mM dNTP | 2 μL |
| 25 mM MgSO₄: | 0.8 μL |
| Forward primer (10 pmol) | 0.5 μL |
| Reverse primer (10 pmol) | 0.5 μL |
| Template of Plasmid GV303-PRPS1 | 1 μL (10 ng) |
| Sterile water | 12.7 μL |
| KOD-PLUS polymerase | 0.5 μL |

Specific PCR program:
95° C. for 10 min (Pre-denaturation)
95° C. for 10 sec (denaturation)
55° C. for 30 sec (annealing)
68° C. for 3 min elongation (30 s/Kb)
30 cycles
68° C. for 10 min.

1 μl of DpnI enzyme was added to PCR product and incubated in water to digest the plasmid template at 37° C. for 1 hour, and subsequently 10 μl of the product was added to *E. coli* TOP10 for amplification. The transformants were confirmed by Sequencing.

Embodiment 4

Purification of PRPS1 Prokaryotic Protein

1. Transformation of pET28a-PRPS1 plasmids into *E. coli* BL21 (DE3)

① 1 μl of pET28a-PRPS1 plasmids and 100 μl of competent *E. coli* BL21 (DE3) cells were sequentially homogenized and placed on ice for 30 minutes, incubated in water at 42° C. for 90 seconds without shaking, and placed on the ice for 2 minutes immediately. After adding with 900 μl of SOC medium, the cells was incubated at 37° C. with shaking at 170 rpm for 1 hour.

② Coating the semi-solid LB agar culture medium containing kanamycin of 50 μg/ml with 1 ml of transformed competent cells. After 16 hours of inverted culturing, when colonies appeared, positive and grown well clones were selected for further experiments.

2. Pilot study of expression:

① Monoclonal from the pET28a-PRPS1 series transformation plate was inoculated into 3 ml of LB (containing antibiotics) and incubated at 37° C. for 10 to 12 hours with shaking at 220 rpm.

② The next day 50 μl bacterial suspension was inoculated into 5 ml LB (containing antibiotics) with a ratio of 1:100 inoculation herein, and incubated at 37° C. for 2 to 3 hours with shaking at 220 rpm until the OD value reaches 0.6.

③ Sampling of control: 2 ml of bacteria suspension was taken and centrifugated for 1 minute at 12000 rpm, and the supernatant was discarded subsequently. 1 ml of PBS solution was added onto the cell pellets and the cell suspension was broken by ultrasonication (200 w for 3 seconds, and pause for 5 seconds, 20 cycles), and then SDS-PAGE Buffer (reduction, 4×) was added in and the mixture was incubated at 100° C. in water for 10 minutes follow by centrifuging at 12000 rpm for 10 minutes. The supernatant was pipetted and stored at −20° C. as a control without induction.

④ The IPTG was added into the remained 3 ml of the bacterial solution to a final concentration of 1 mM, and the solution was incubated at 16° C. for 16 hours with shaking at 220 rpm. Then the solution was centrifuged for 1 minute at 12000 rpm and the supernatant was discarded, and the cell pellets were broken by ultrasonication and samples were stored at −20° C.

⑤ The above-mentioned samples were identified by SDS-PAGE electrophoresis.

3. PRPS1 overexpression

① Monoclonal was inoculated into 3 ml of LB (containing antibiotics) and incubated at 37° C. for 10 to 12 hours with shaking at 220 rpm.

② Expanding culture: the ratio of inoculation is 1:100, that is, 20 ml of bacterial suspension was added into 2 L of LB culture medium (comprising antibiotics) and incubated at 37° C. for 4 to 5 hours with shaking at 220 rpm until the OD value reaches 0.6-0.8.

③ Sampling of control: 2 ml of bacteria suspension was taken and centrifugated for 1 minute at 12000 rpm, and the supernatant was discarded subsequently. 1 ml of PBS solution was added onto the cell pellets, and the cell suspension was broken by ultrasonication (200 w for 3 seconds and pause for 5 seconds, 20 cycles), and then SDS-PAGE Buffer (reduction, 4×) was added in and mixture was incubated at 100° C. in water for 10 minutes follow by centrifuging at 12000 rpm for 10 minutes. The supernatant was pipetted and stored at −20° C. as a control without induction.

④ After remained bacterial suspension was incubated at 16° C. for further 1 hour with shaking at 220 rpm, IPTG was added to the bacterial suspension to a final concentration of 1 mM, and the bacterial suspension was incubated at 16° C. for 16 hours with shaking at 220 rpm. Then the suspension was centrifuged at 4° C. for 10 minutes at 6000 rpm and the supernatant was removed. 5 ml of the bacteria was taken for identification of expression (sample at 16° C.), and the rest cell pellets were stored at −80° C.

⑤ Said series samples of PRPS1 were ultrasonicated separately and then identified by SDS-PAGE electrophoresis (in consistent with ⑤ of "Pilot study of expression").

Figure 4:
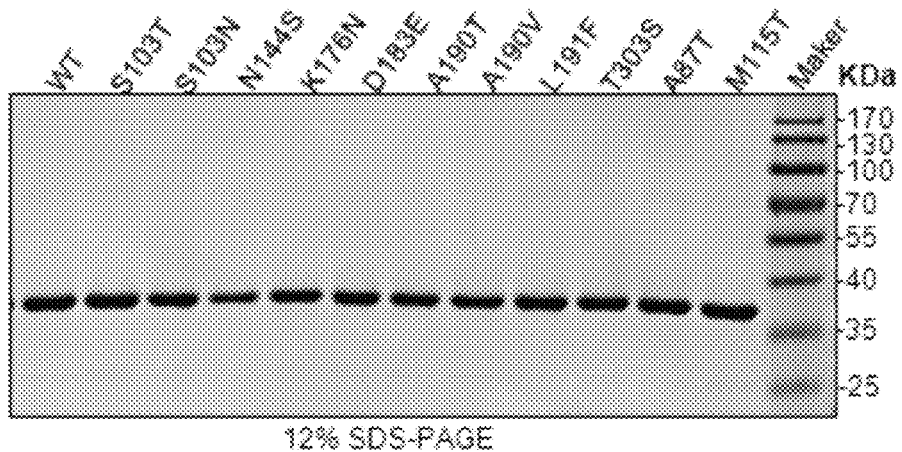
FIG. 4 SDS-PAGE results of purified wild-type and mutants PRPS1 proteins.

4. Purification of PRPS1 protein: the bacteria suspension which was broken by ultrasonication was then purified by nickel column in the AKTA-purifier system to obtain series of PRPS1 protein. The expression and purity of series of PRPS1 protein were identified by SDS-PAGE electrophoresis, as shown in FIG. 4. The series of PRPS1 proteins were quantified by BCA protein quantitative kit from Beyotime, and the PRPS1 wild-type protein was obtained with sequence as set forth in SEQ ID NO. 2 in Sequence Listing.

Embodiment 5

Construction of Eukaryotic Expression Vector for PRPS1 Mutant Gene

Figure 5:
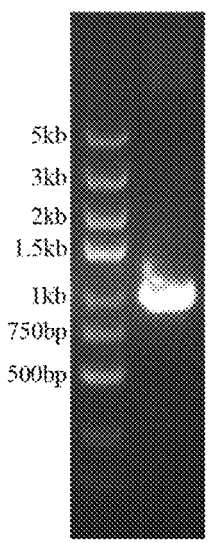
FIG. 5 Agarose gel electrophoresis results of amplified PCR products from PRPS1 wild-type.

1. Acquisition of the target gene fragment: primers for amplifying PRPS1 wild-type including forward primer 5' GAGGATCCCCGGGTACCGGTCGCCACCATGCCG AATATCAAAATC 3' (SEQ ID NO: 19) and reverse primer 5' TCCTTGTAGTCCATACCGTGGTG GTGGTGGTGGTGCTCGAGTAAAG 3' (SEQ ID NO: 20) were designed according to the PRPS1 sequence provided by NCBI (gene ID: 5631, NM 002764). Primers contains exchanged-pairing base, cleavage site, and 5'end sequence of target gene used for PCR capturing target gene. Having a product size of 1022 bp, PRPS1 was captured by PCR using Pet-28a-PRPS1 as plasmid template, and the PCR product was shown in FIG. 5.

PCR System:

| | |
|---|---|
| 10 × KOD Buffer | 2 μL |
| 2 mM dNTP | 2 μL |
| 25 mM MgSO$_4$: | 0.8 μL |
| Forward primer (10 pmol) | 0.5 μL |
| Reverse primer (10 pmol) | 0.5 μL |
| Plasmid pET-28a-PRPS | 1 μL (10 ng) |
| Sterile water | 12.7 μL |
| KOD-PLUS polymerase | 0.5 μL |

PCR Reaction Program:
 95° C. for 10 min (Pre-denaturation)
 95° C. for 10 sec (denaturation)
 55° C. for 30 sec (annealing)
 68° C. for 3 min elongation (30 s/Kb)
 30 cycles
 68° C. for 10 min.

1 μl of DpnI enzyme was added to the PCR product and the plasmid template was digested by incubating in water at 37° C. for 1 hour, and 10 μl of digested product was added to E. coli TOP10 for following amplification. The transformants were sequenced to confirm whether the mutants were constructed successfully.

2. Linearization of the virus expression vector: The GV303 viral vector was reacted with the restriction endonuclease AgeI (Genechem).

3. Construction of recombinant plasmid: The PCR product of Step 1 was exchanged into the linearized viral vector using In-Fusion™ PCR Cloning Kit kit from Clontech, and the recombinant GV303-PRPS1 was amplified by E. coli TOP10.

4. Identification of recombinant plasmids by enzyme digestion: The recombinant was identified by restriction endonuclease Hind III, and the recombinant will be a positive clones if 354 bp fragment was identified.

5. Construction of plasmid of PRPS1 mutant: 9 lentivirus expression vectors containing PRPS1 mutants: GV303-PRPS1-S103T, GV303-PRPS1-S103N, GV303-PRPS1-N144S, GV303-PRPS1-T303S, GV303-PRPS1-K176N, GV303-PRPS1-D183E, GV303-PRPS1-A190T, GV303-PRPS1-A190V and GV303-PRPS1-L191F were constructed by PCR using KOD-Plus DNA polymerase from TOYOBO with GV303-PRPS1 as plasmid template, and PCR primers were shown in Table 5.

TABLE 5

Sequence Listing of PCR primers of PRPS1 mutants

| | Forward primers (5'-3') | Reverse primers (5'-3') |
|---|---|---|
| S103T | GAAAGATAAGACCCGGGCGCC AATCTCAGCC (SEQ ID NO: 21) | GGCGCCCGGGTCTTATCTTTC TTATCCTGC (SEQ ID NO: 22) |
| S103N | GAAAGATAAGAACCGGGCGC CAATCTCAGCC (SEQ ID NO: 23) | GGCGCCCGGTTCTTATCTTTC TTATCCTGC (SEQ ID NO: 24) |

TABLE 5-continued

Sequence Listing of PCR primers of PRPS1 mutants

| | Forward primers (5'-3') | Reverse primers (5'-3') |
|---|---|---|
| N144S | CCAGTAGACAGTTTGTATGCA GAGCCGGC (SEQ ID NO: 25) | GCATACAAACTGTCTACTGG GATACAAAAAAG (SEQ ID NO: 26) |
| T303S | CATCAGGAGAAGTCACAATGG AGAATCCGT (SEQ ID NO: 27) | CCATTGTGACTTCTCCTGATG GCTTCTGC (SEQ ID NO: 28) |
| K176N | GGAGCTAACAGAGTGACCTCC ATTGC (SEQ ID NO: 29) | GTCACTCTGTTAGCTCCACC AGCATC (SEQ ID NO: 30) |
| D183E | CCATTGCAGAGAGGCTGAATG TGGACTTTGC (SEQ ID NO: 31) | CATTCAGCCTCTCTGCAATG GAGGTCACTC (SEQ ID NO: 32) |
| A190T | GTGGACTTTACCTTGATTCACA AAGAACGGA (SEQ ID NO: 33) | GTGAATCAAGGTAAAGTCCA CATTCAGCCTG (SEQ ID NO: 34) |
| A190V | GTGGACTTTGTCTTGATTCACA AAGAACGGA (SEQ ID NO: 35) | GTGAATCAAGACAAAGTCCA CATTCAGCCTG (SEQ ID NO: 36) |
| L191F | GTGGACTTTGCCTTCATTCACA AAGAACGGA (SEQ ID NO: 37) | GTGAATGAAGGCAAAGTCCA CATTCAGCCTG (SEQ ID NO: 38) |

Embodiment 6

Preparation of Reh Cells Expressing PRPS1 Mutant Genes
Preparation of Virus

1. HEK293T cells were seeded into 10 cm dishes 24 hours before transfection and the transfection can be initiated when the cell density reaches 50% to 80% in next day.

2. Prepare the mixture of DNA-Opti-MEM and Fugene-6-Opti-MEM (one dish of cells).

TABLE 6

| | Quanity of plasmid for tranfection | Opti-MEM | Fugene-6 | Opti-MEM |
|---|---|---|---|---|
| pMD2.G | 1.1 µg | 11 µl | 19.8 µl | 220 µl |
| psPAX2 | 1.1 µg | | | |
| GV303 viral plasmids expressing PRPS1 mutant genes | 1.65 µg | | | |

Transfection reagent Fugene-6 and Opti-MEM from Promega were mixed and allowed to stand for 5 minutes. DNA-Opti-MEM and Fugene-6-Opti-MEM were mixed and allowed to stand for 15 minutes.

3. During the standing process of mixture, replaced the dish culturing with HEK293T by fresh antibiotic-free medium.

4. The mixture was stood for 15 min, and added to the dish culturing with HEK293T cells by 233 µl/dish. The culture medium was mixed cruciformly, that is, shake the medium up, down, left and right for 5 times.

5. Cells were incubated under conditions of 37° C., 5% $CO_2$ for 24 hours, and the culture medium was exchanged with fresh medium by 15 ml/dish. Cells were further cultured for another 72 hours and the medium containing virus was collected.

6. The collected supernatant containing virus was transferred to Amicon Ultra-15 100 KD ultrafiltration tubes and centrifuged at 4° C. for 30 minutes to obtain concentrated virus solution.

7. HEK293T cells were infected by gradient dilution of the virus solution and the titer of the virus was calculated based on the number of post-infected green fluorescent cells.

Viral Infection

1. Cells inoculation: Reh cells were counted and seeded into 12-well plates, with each well inoculated $3 \times 10^5$ cells.

2. Concentrated virus supernatant (MOI=10) and polybrene at a final concentration of 8 µl/ml were added to each well simultaneously and the cells were further cultured in incubator for 24 hours. Then the culture medium of the cells was exchanged to fresh complete medium followed by observing the fluorescence under a microscope after 48 hours.

3. Flow sorting of cells: The cells were infected by virus for 72 hours. Reh cells with green fluorescence were harvested by Beckman's flow cytometer Moflo XDP, and then cultured for enlargement.

Figure 6:
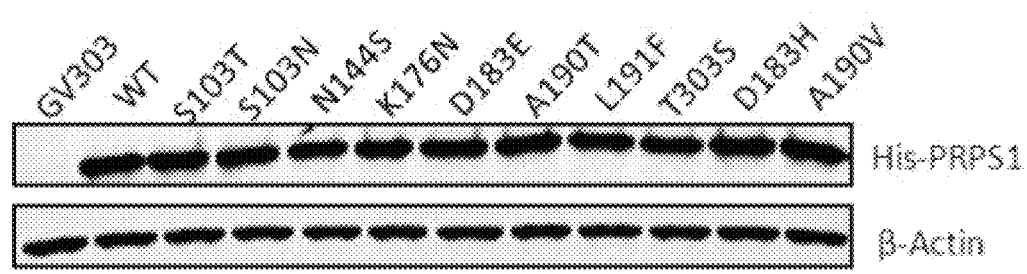
FIG. 6 Western-blots of stable Reh cell line expressing PRPS1 wild-type and mutants.

4. The sorted Reh cells were collected and the expression of PRPS1 wild-type and PRPS1 mutant type was identified by Western blot to confirm whether the stable cell line was successfully constructed. The experimental results are shown in FIG. 6. The following nine stable cell lines: Reh-PRPS1-S103 T, Reh-PRPS1-S103N, Reh-PRPS1-N144S, Reh-PRPS1-T303 S, Reh-PRPS1-K176N, Reh-PRPS1-D183E, Reh-PRPS1-A190T, Reh-PRPS1-A190V and Reh-PRPS1-L191F were obtained.

The stable cell line Reh-PRPS1-WT, of which stably overexpresses wild type PRPS1, was constructed using the GV303-PRPS1 lentiviral expression vector in the same manner as described above.

Embodiment 7

Drug Susceptibility Test of 6-MP

Reh cells are a strain of human acute B lymphoblastic leukemia. The susceptibility of the PRPS1 mutant to the chemotherapeutic drug 6-MP was determined by the survival rate of Reh cells expressing different PRPS1 mutant genes which were treated by chemotherapeutic drug 6-MP, wherein the process comprises steps of
(i) Cell inoculation: Reh cells expressing the PRPS1 wild-type and all kinds of PRPS1 mutants were counted and seeded into 96-well plates with inoculated $10^4$ cells per well. Five parallel wells were designed.
(ii) Cell treatment: the drug 6-MP was 3 folds diluted gradiently with an initial concentration of 100 μg/ml to obtain 10 gradient dilutions. Drugs were added into 96-well plates with grown cells and incubated at 37° C. for 72 hours.
(iii) Cell viability test: after 72 hours, 50 μl of CellTiter-Glo reagent (Promega) was added to each well and incubated at room temperature for 10 minutes. The chemiluminescence values were read in a microplate reader (Biotek).
(iv) $IC_{50}$ calculation: $IC_{50}$ values of drug were calculated using Graphpad 5.0 software and differences between groups were compared.

Figure 7:
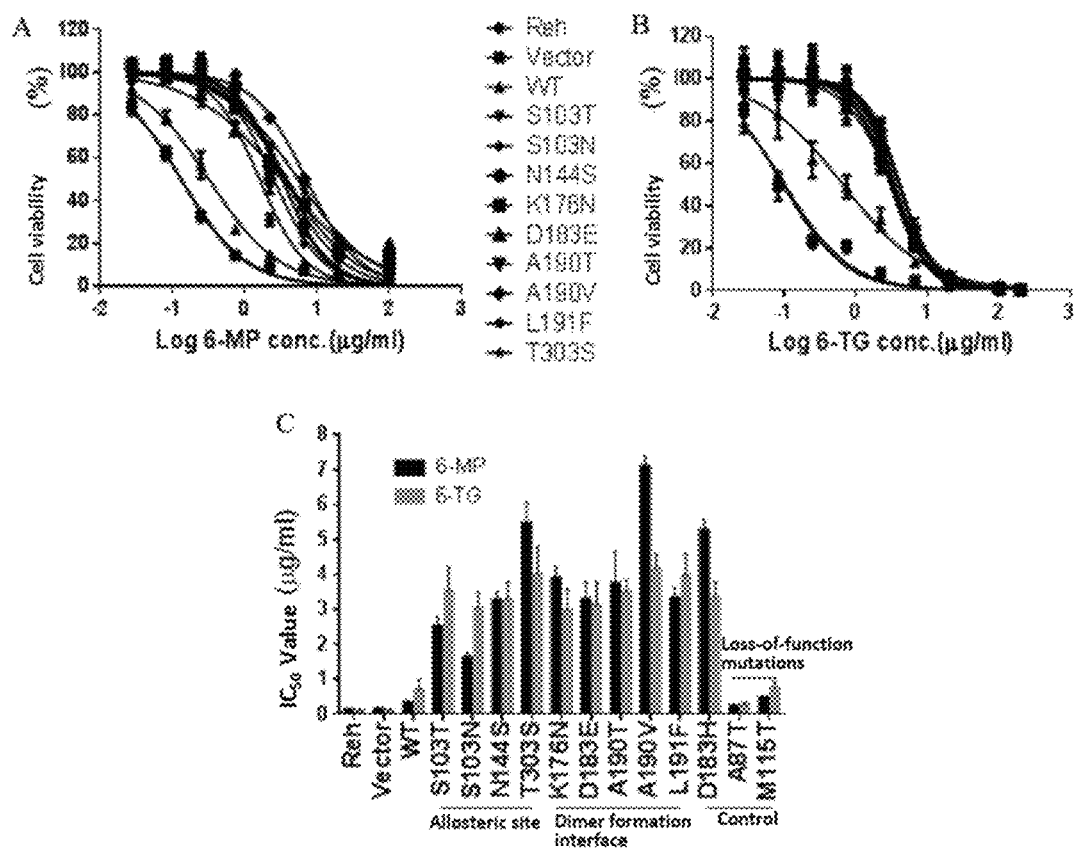
FIG. 7 Drug susceptibility of stable Reh cell line to 6-MP and 6-TG, of which the cell lines expresses PRPS1 wild-type and mutants.

The experimental results are shown in FIG. 7. Compared with the control group expressing empty-load, the $IC_{50}$ values of the PRPS1 mutant genes in the experimental group were significantly increased, which indicates that the survival rate of cells containing the PRPS1 mutant in the experimental group is significantly increased after 6-MP treatment, i.e. drug resistance of cells is increased significantly.

Embodiment 8

Drug Susceptibility Test of 6-TG

The susceptibility of the PRPS1 mutant to the chemotherapeutic drug 6-TG was determined by the survival rate of Reh cells expressing different PRPS1 mutant genes which were treated by chemotherapeutic drug 6-TG, in which the process comprises steps of
(i) Cell inoculation: Reh cells expressing the PRPS1 wild-type and all kinds of PRPS1 mutants were counted and seeded into 96-well plates with inoculated $10^4$ cells per well. Five parallel wells were set up.
(ii) Cell treatment: the drug 6-TG was 3 folds diluted gradiently with an initial concentration of 100 μg/ml to obtain 10 of gradient dilutions. Drug were added into 96-well plates with grown cells and incubated at 37° C. for 72 hours.
(iii) Cell viability test: after 72 hours, 50 μl of CellTiter-Glo reagent (Promega) was added to each well and incubated at room temperature for 10 minutes. The chemiluminescence values were read in a microplate reader (Biotek).
(iv) $IC_{50}$ calculation: $IC_{50}$ values of drug were calculated using Graphpad 5.0 software and differences between groups were compared.

The experimental results are shown in FIG. 7. Compared with the control group expressing empty load, the $IC_{50}$ values of the PRPS1 mutant genes in the experimental group were significantly increased indicating that the survival rate of cells containing the PRPS1 mutant in the experimental group was significantly increased after 6-tg treatment, i.e. drug resistance of cells is increased significantly.

Embodiment 9

Identification of Cells Apoptosis
(i) Cell inoculation: Reh cells expressing the PRPS1 wild-type and various PRPS1 mutants were counted and seeded into 12-well plates with inoculated $3\times10^5$ cells per well. Duplicated wells were set up.
(ii) Cell treatment: the drug 6-MP or 6-TG with concentration of 10 μg/ml was added to a 12-well plate with grown cells and incubated at 37° C. for 72 hours.
(iii) Cell staining: After 72 hours, the cells were collected by centrifugation, washed with PBS buffer, added in Annex I-V and 7-AAD dye labeled with PE from BD, and incubated for 15 minutes at room temperature. The cells were centrifuged to discard the supernatant and washed twice with PBS.
(iv) Identification by Flow Cytometer: proportion of cell apoptosis was determined using Flow Cytometer from Canto II BD.

Figure 8:
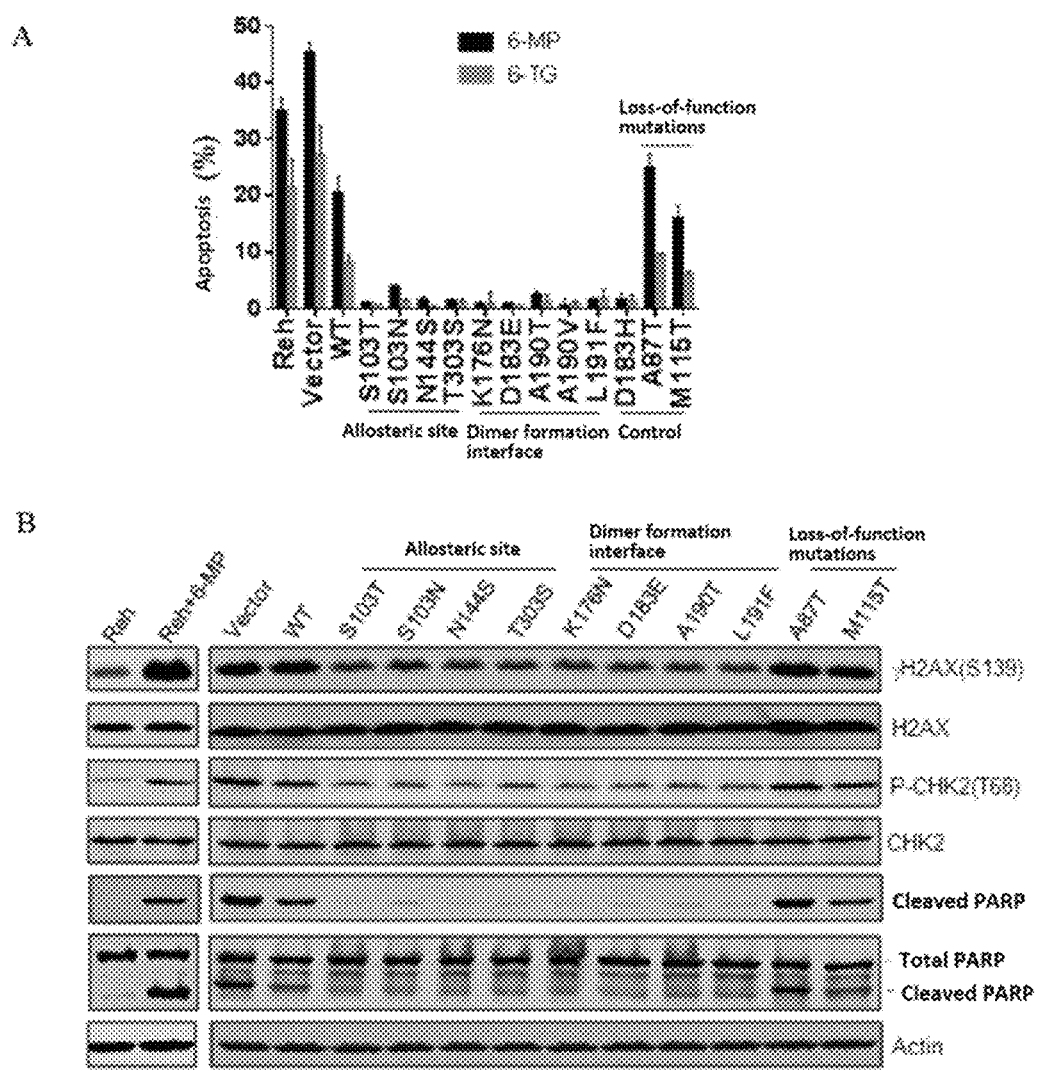
FIG. 8 The cell apoptosis effects of 6-MP and 6-TG on stable Reh cell line expressing PRPS1 wild-type and mutants.

The experimental results are shown in FIG. 8. Compared with the control group expressing empty load, the apoptotic ratio of cells expressing PRPS1 mutant genes in the experimental group was significantly down-regulated, indicating that the livability of the PRPS1 mutant cells in the experimental group was significantly increased after 6-MP or 6-TG treatment, i.e. drug resistance of cells is increased significantly.

Embodiment 10

Identification of Metabolites of Intracellular Chemotherapeutic Drugs 6-MP/6-TG.

6-MP is a prodrug and needs to be undergone metabolic reactions in vivo to form TIMP and TGMP before it works, as shown in FIG. 9C. The identification procedure is as follows:
(i) Cell inoculation: Reh cells expressing the PRPS1 wild-type and various PRPS1 mutants were counted and seeded into 6 cm culture dish with inoculated $3\times10^6$ cells in each plate.
(ii) Cell treatment: 10 μM chemotherapy drug 6-MP was added into each 6 cm culture dish and treated for 4 hours;
(iii) Cell collection: The cells were transferred to a centrifuge tube, centrifuged at 3,000 g for 5 minutes to remove the supernatant, and lysed at $3\times10^6$ cells per 200 μl 80% methanol;
(iv) The amounts of metabolites from chemotherapeutic drugs 6-MP, TIMP, TGMP, r-MP, r-TG and r-MMP were measured by LC-MS (ABI 5500 Qtrap coupled with Waters Acquity UPLC), and standard curve for quantification was made using TIMP (Jean Bioscience, cat #NU (Sigma, cat #854126), r-TG (Sigma, cat #858412), r-MMP (Sigma, cat #M4002) respectively.

Figure 9:
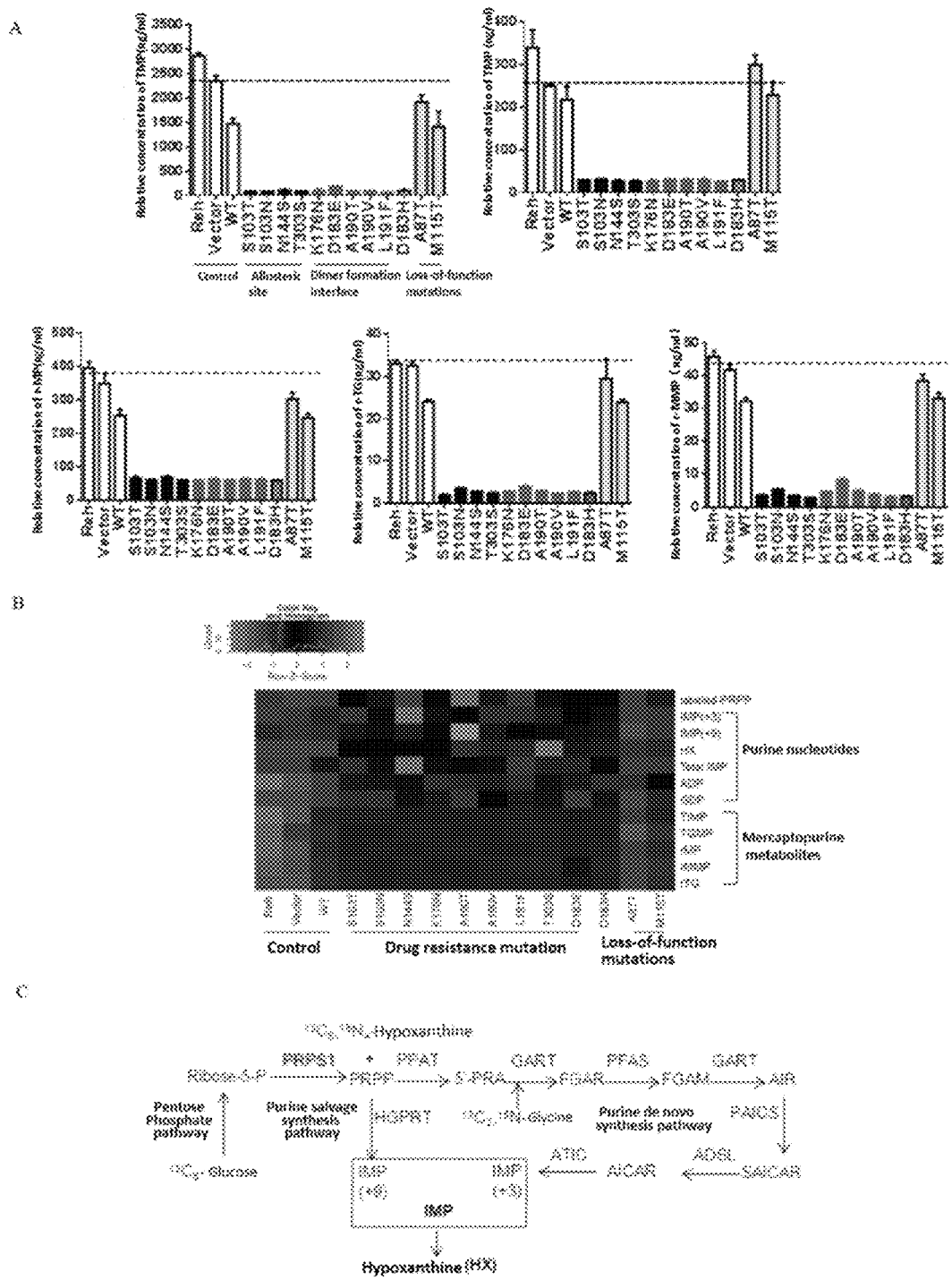
FIG. 9 Detection results of intracellular metabolites of chemotherapeutic drugs 6-MP/6-TG.

The experimental results are shown in FIG. 9. For those mutants in experimental groups being treated with 6-MP, the contents of chemotherapeutic drugs 6-MP metabolites TIMP, TGMP and r-MP, r-TG and r-MMP in cells were significantly lower than those in control group.

Embodiment 11

Detection of PRPS1 Enzyme Activity
(i) Cell culture: Reh cells expressing the PRPS1 wild-type and various PRPS1 mutants were counted and seeded into 6 cm culture dish, and $3\times10^6$ cells were inoculated in each well.
(ii) Cell treatment: The cells were resuspended the next day using glucose-free medium (Gibco, cat #11879-020), and 10 mM glucose labeled with $^{13}C_6$ was added into each 6 cm culture dish (Cambridge isotope laboratories, cat #CLM-1396-1) and label for 5 minutes;
(iii) Cell collection: The cells were transferred to a centrifuge tube, centrifuged at 3,000 g for 5 minutes, the supernatant was removed, and the cells were lysed using $3\times10^6$ cells/200 μl 80% methanol;
(iv) The level of $^{13}C_5$-PRPP was detected by LC-MS (ABI 5500 Qtrap coupled with Waters Acquity UPLC), and standard curve quantification was made using PRPP (sigma, cat #P8296).

Figure 10:
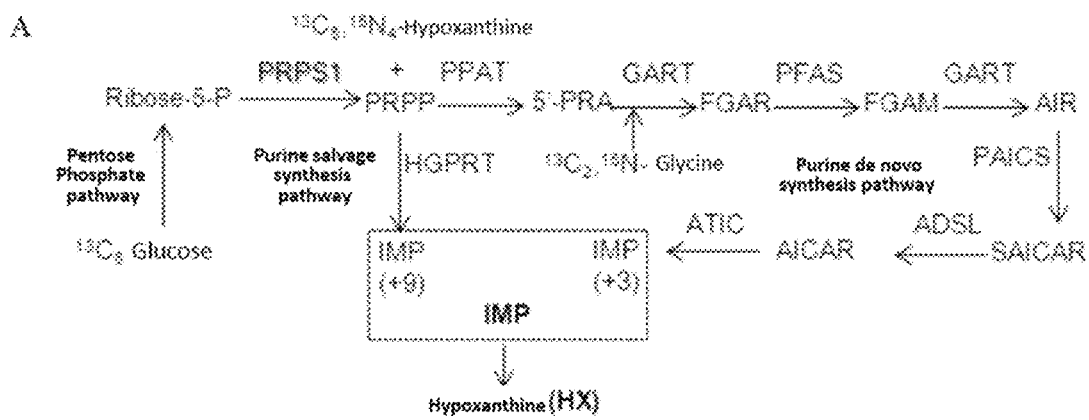
FIG. 10 Detection results of PRPS1 enzyme activity of wild-type and mutants expressing PRPS1.
Figure 10:
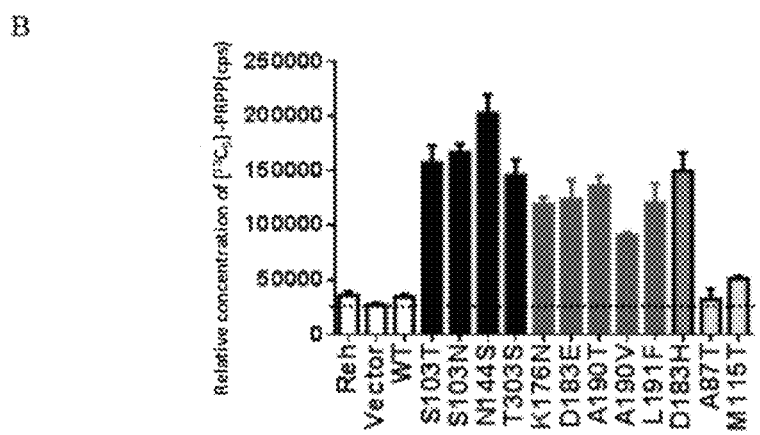

The experimental results are shown in FIG. 10. Compared with the control group expressing empty load, the concentration of PRPP product catalyzed by each PRPS1 mutant gene in the experimental group was significantly increased which confirms that PRPS1 enzyme activity of each mutant in experimental group was significantly increased.

Embodiment 12

Figure 11:
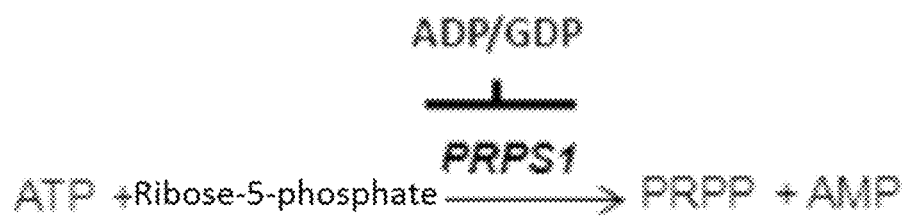
FIG. 11 Diagram of PRPS1 subjecting to feedback regulation of ADP and GDP.

Determination of Feedback Regulation of Nucleotide ADP, GDP on PRPS1 Activity
1. In Vitro Protein Level
(i) Establishment of enzymatic reaction catalyzed by PRPS1, as shown in FIG. 11. ATP (Item No. A7699), ADP (Item No. A2754), GDP (Item No. G7172) and ribose-5-phosphate (Item No. R7750) were purchased from Sigma. The reaction system comprised 50 mM Tris pH 7.5, 2 mM phosphate, 1 mM DTT, 10 mM MgCl2, 0.5 mM ribose-5-phosphate, 0.5 mM ATP and PRPS1 protein.
(ii) Inhibition of GDP/ADP on PRPS1 protein activity: 3 times gradient dilution of the GDP/ADP with an initial concentration of 5 mM And 15 μL of PRPS1 in vitro enzyme reaction system was prepared, added into 384-well plate, and reacted at 37° C. for 30 minutes. Then 10 μL of Kinase-Glo reagent (Item No. V3722) from Promega was added reacted at 37° C. for 15 minutes to terminate the reaction. The chemiluminescence values can be read in a microplate reader, and the inhibition of GDP/ADP on PRPS1 protein activity was calculated by Graphpad 5.0.

Figure 12:
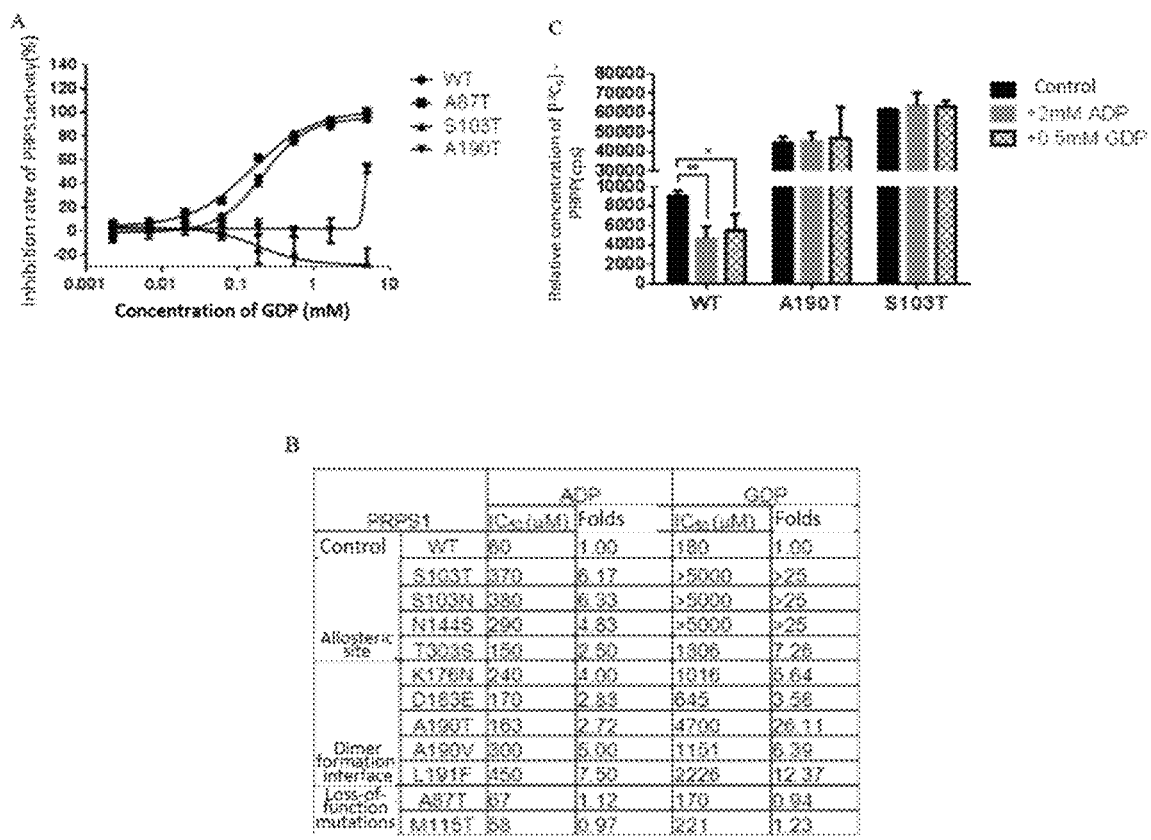
FIG. 12 Inhibitory effects of GDP/ADP on PRPS1's protein activity.

The experimental results were shown in FIG. 12A, 12B. It can be seen that the inhibition of GDP/ADP on PRPS1 mutants S103T, 5103N, N144S, T303S, K176N, D183E, A190T, A190V, L191F were significantly lower than that on PRPS1 wild-type, and the known loss-of-function mutants A87T and M115T has no significant difference with wild-type, that is, the relapse-specific mutation of PRPS1 escapes the negative feedback inhibition of the nucleotide GDP/ADP on PRPS1 activity which is a gain-of-function mutant.
2. Cell Level In the present invention, the intracellular activity of PRPS1 was detected by means of isotope labeling in combination with the technologies of cell biology and metabolomics, and based on this, the effect of nucleotide GDP/ADP on PRPS1 activity was evaluated. The preferred embodiment is as follows:
(i) Cell culture: Reh cells expressing the PRPS1 wild-type and various PRPS1 mutants were counted and seeded into 6 cm culture dish, and $3\times10^6$ cells were inoculated in each well.
(ii) Cell treatment: 2 mM ADP or 0.5 mM GDP was added to the culture dish and cells were treated for 4 hours, after that, the cells were resuspended using glucose-free medium (Gibco, cat #11879-020), and 10 mM glucose labeled with $^{13}C_6$ was added into each 6 cm culture dish (Cambridge isotope laboratories, cat #CLM-1396-1) and labeled for 5 minutes.
(iii) Cell collection: The cells were transferred to a centrifuge tube, centrifuged at 3,000 g for 5 minutes, the supernatant was removed, and the cells were lysed using $3\times10^6$ cells/200 μl 80% methanol.
(iv) The level of $^{13}C_5$-PRPP was detected by LC-MS (ABI 5500 Qtrap coupled with Waters Acquity UPLC), and standard curve quantification was made using PRPP (sigma, cat #P8296). The activity of PRPS1 was determined according to the level of PRPP.

The experimental results are shown in FIG. 12C. The concentration of PRPP expressed in wild-type experimental group was decreased after adding the nucleotide GDP/ADP and the concentration of PRPP product catalyzed by each PRPS1 mutant gene in experimental group was not affected by nucleotide GDP/ADP indicating that the enzyme activity of the PRPS1 mutant in the cells expressing the PRPS1 mutant gene in the experimental group was not feedback-regulated by the nucleotide GDP/ADP.

Embodiment 13

Activity Detection of Purine Metabolic Pathway
In the present invention, the activity of purine de novo synthesis pathway and salvage synthesis pathway in cells were detected by means of isotope labeling in combination with the technologies of cell biology and metabolomics. The preferred embodiment is as follows:
(i) Cell culture: Reh cells expressing the PRPS1 wild-type and various PRPS1 mutants were counted and seeded into 6 cm culture dish, and $3\times10^6$ cells were inoculated in each well.
(ii) Cell treatment: The cells were resuspended the next day using amino acid-free medium (Gibco, cat #ME100031L1). De novo synthesis pathway was labeled with 20 μl/ml $^{13}C_2$ and $^{15}N$-glycine (Sigma, cat #489522), respectively, for 4 hours, and salvage synthesis pathway was labeled with 2 μM $^{13}C_5$ and $^{15}N_4$-hypoxanthine (Cambridge isotope laboratories, cat #489522), respectively, for 1 hour.
(iii) Cell collection: The cells were transferred to a centrifuge tube, centrifuged at 3,000 g for 5 minutes, the supernatant was removed, and each of $3\times10^6$ cells were lysed using 200 μl 80% methanol.
(iv) The level of nucleotide labeled with $^{13}C_2$, $^{15}N$-hypoxanthine (IMP+3), and $^{13}C_5$, $^{15}N_4$-hypoxanthine (IMP+9) was detected by LC-MS (ABI 5500 Qtrap coupled with Waters Acquity UPLC), and standard curve quantification was made using IMP (sigma, cat #I4625).

Figure 13:
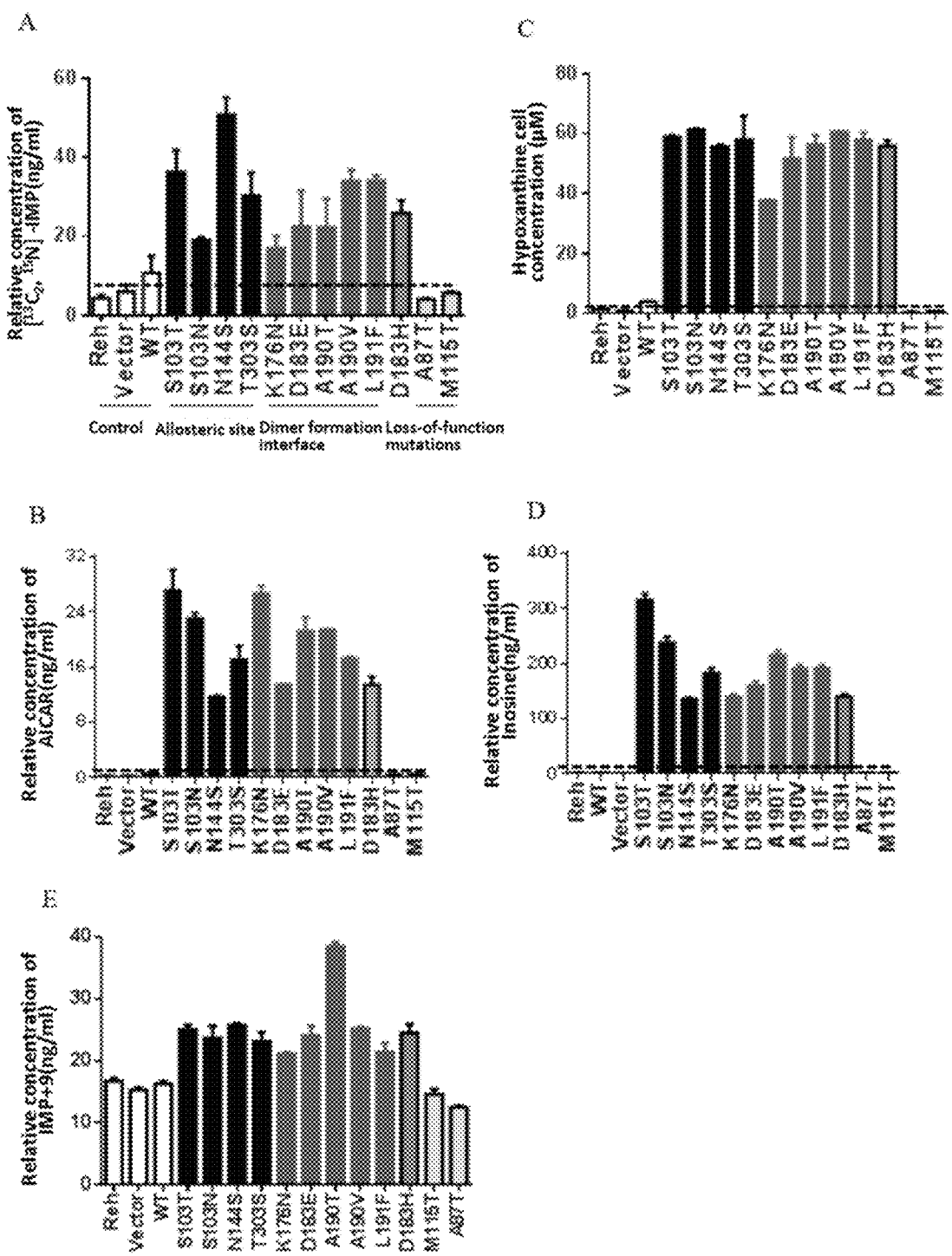
FIG. 13 Content determination of intracellular products in purine metabolic pathway.
Figure 18:
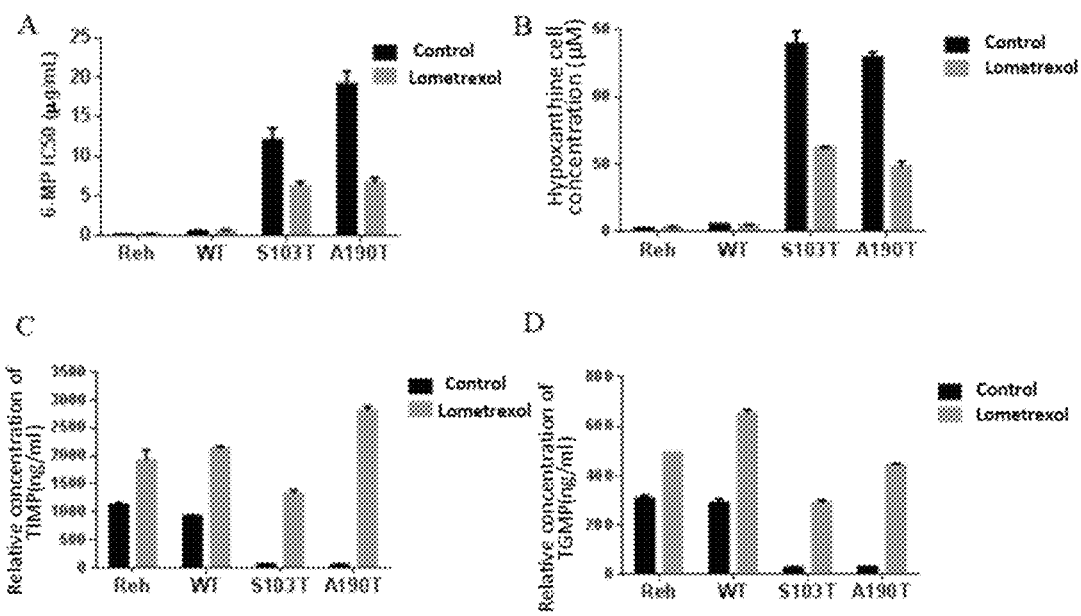
FIG. 18 Lometrexol reverses the 6-MP resistance resulting from PRPS1 gene mutant.

The experimental results are shown in FIG. 13, FIG. 9B and FIG. 18. The concentration of IMP+3 and IMP+9 in Reh cells expressing PRPS1 drug resistance mutations were significantly increased compared to that in Reh cells expressing empty load and PRPS1 wild-type, i.e. the activity of purine de novo synthesis pathway and salvage synthesis pathway were significantly increased.

Embodiment 14

Determination of the Contents of Hypoxanthine, AICAR and Inosine in Samples.
In the present invention, the content of hypoxanthine in cells was detected by LC-MS technology in combination with the technologies of cell biology and metabolomics. The preferred embodiment is as follows:
(i) Cell culture: viruses of PRPS1 wild-type and various mutants were transfected into human Reh cells (see Embodiment 4 herein), and cells were incubated.

(ii) Cell counting: when the number of cells per well reached $5\times10^6/5$ ml, samples were taken according to the number of cells required for the experiment.

(iii) Cell collection: cells were pipetted out from the well and centrifuged at 1500 rpm to remove the supernatant. The cells were washed with PBS once, and centrifuged again (500 g). Removed the supernatant.

(iv) Cell lysis: the cells were lysed using 200 μl 80% methanol per $3\times10^6$ cells.

(v) The lysed cells were centrifuged by 14,000 g at 4° C. for 10 minutes, and then the supernatant was transferred to a 1.5 ml EP tube.

(vi) The contents of hypoxanthine, AICAR and Inosine were detected by LC-MS technology (ABI 5500 Qtrap coupled with Waters Acquity UPLC), and standard curves for absolute quantification were made using $^{13}C_5$, $^{15}N_4$-hypoxanthine (Cambridge isotope laboratories, cat #489522), AICAR (sigma, cat #A9978) and Inosine (Sigma, cat #I4125), respectively.

The experimental results are shown in FIG. 13. Compared to the cells expressing empty vector and PRPS1 wild-type in the control group, the concentrations of hypoxanthine, AICAR and Inosine in Reh cells expressing PRPS1 drug resistance mutations in experimental group were significantly increased.

Embodiment 15

Nucleic Acid Drugs Targeting Purine Synthesis Pathway

Preparation of lentivirus LV-CRISPR-ATIC and LV-CRISPR-GART for purine de novo synthesis pathway and its application in reversing drug resistance of 6-MP caused by PRPS1 gene mutation.

(i) Construction of CRISPR Lentiviral Vector: based on the sequences of GART and ATIC and the design criteria of CRISPR, the corresponding sequences were designed as follows: CRISPR-ATIC: TGAATCTGGTCGCTTCCGGA (SEQ ID NO: 40), CRISPR-GART: GCAGCCCGAGTACTTATAAT (SEQ ID NO: 39). The corresponding sequences were constructed into CRISPR lentiviral vector (Addgene, cat #49535) to form lentiviral vector, lentiCRISPR-ATIC and lentiCRISPR-GART.

(ii) Lentivirus LV-CRISPR-ATIC and LV-CRISPR-GART expressing CRISPR RNA corresponding to gene ATIC and GART were obtained by packaging according to reported method (Shalem O, Sanjana N E, Hartenian E, Shi X, Scott D A, Mikkelsen T S, Heckl D, Ebert B L, Root D E, Doench J G, Zhang F, *Science.* 2014 Jan. 3; 343(6166):84-7. doi: 10.1126/science.1247005. Epub 2013 Dec. 12).

(iii) Cell lines Reh-PRPS1-S103T and Reh-PRPS1-A190T were infected by packaged lentivirus with empty load lentivirus LV-CRISPR-ATIC and LV-CRISPR-GART, respectively, to form stable cell line, of which the MOI of lentivirus was 10. Then 8 μg/ml of polybrene was added in. After 24 hours, the culture medium was changed and the cells were cultured for further 48 hours, and then cells were treated with 0.8 μg/ml of puromycin for resistance screening for one week to form the following stable cell lines: the control cell line Reh-LV-CRISPR, Reh-S103T-CRISPR-ATIC, Reh-S103T-CRISPR-GART, Reh-A190T-CRISPR-ATIC and Reh-A190T-CRISPR-GART.

(iv) Cell treatment: The drug 6-MP was diluted and added into 96-well plate plated with cell lines as described in step (iii). Five parallel wells were set up for each cell line to detect the susceptibility of lentiviral infected cells to 6-MP. The preferred embodiment is as Embodiment 8.

Figure 14:
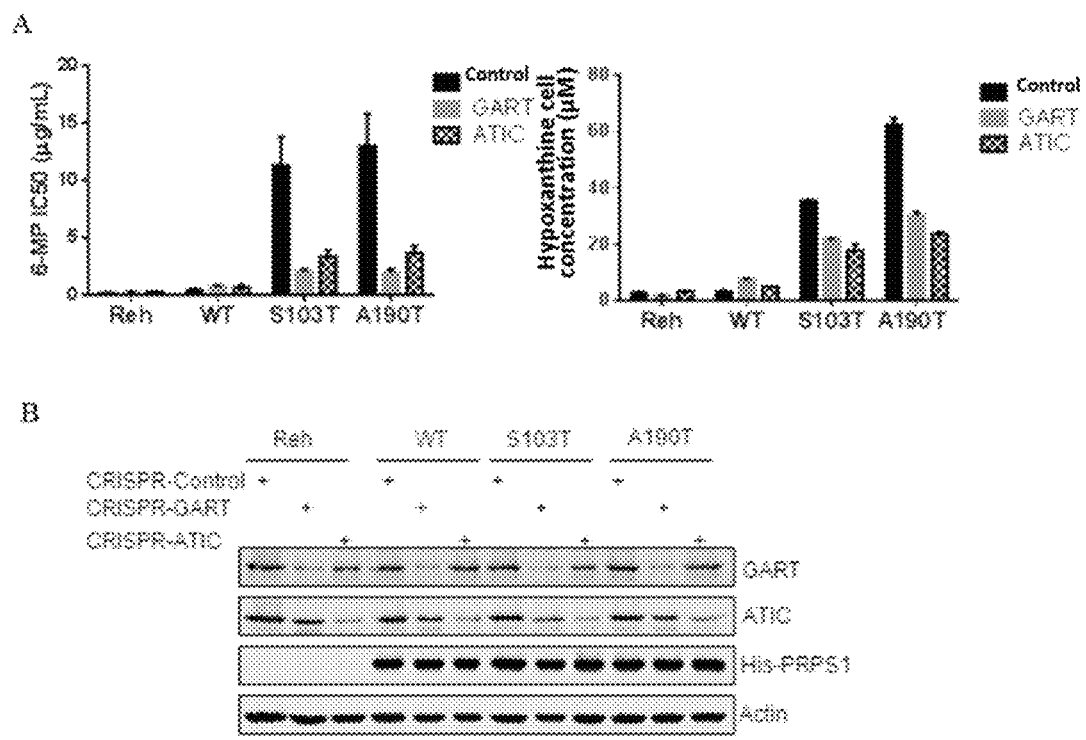
FIG. 14 Inhibitory effect of CRISPR guide RNA targeting purine synthesis pathway on the drug resistance of PRPS1 S103T and A190T mutants.

As shown in FIG. 14, the $IC_{50}$ values of 6-MP in cell lines Reh-S103T-CRISPR-ATIC, Reh-S103T-CRISPR-GART, Reh-A190T-CRISPR-ATIC and Reh-A190T were significantly decreased compared with the control cell line Reh-LV-CRISPR infected by virus with empty load, indicating that the resistance to drug 6-MP was significantly reduced.

Embodiment 16

Addition of exogenous purine affects the resistance of Reh cells to chemotherapeutic drug 6-MP.

The steps for determining the impacts of exogenous purine on drug susceptibility of Reh cells are as follows:

(i) Cell inoculation: Reh cells were counted and seeded into 96-well plates, with $10^4$ cells inoculated in each well. Five parallel wells were set for each group.

(ii) Cell treatment: 10 μM, 50 μM, 100 μM hypoxanthine (HX) or hypoxanthine (IMP) were added to each group for pretreatment for 1 hour. Then the drug 6-TG was 3 times diluted gradiently with an initial concentration of 100 μg/ml to obtain 10 gradient dilutions. Finally, the gradient dilutions were added into 96-well plates with plated cells and incubated at 37° C. for 72 hours.

(iii) Cell viability test: subsequently, 50 μl of CellTiter-Glo reagent (Promega) was added to each well and incubated at room temperature for 10 minutes. The chemiluminescence values were read in a microplate reader (Biotek).

(iv) $IC_{50}$ calculation: $IC_{50}$ values of drug were calculated using Graphpad 5.0 software and the differences between groups were compared.

Figure 15:
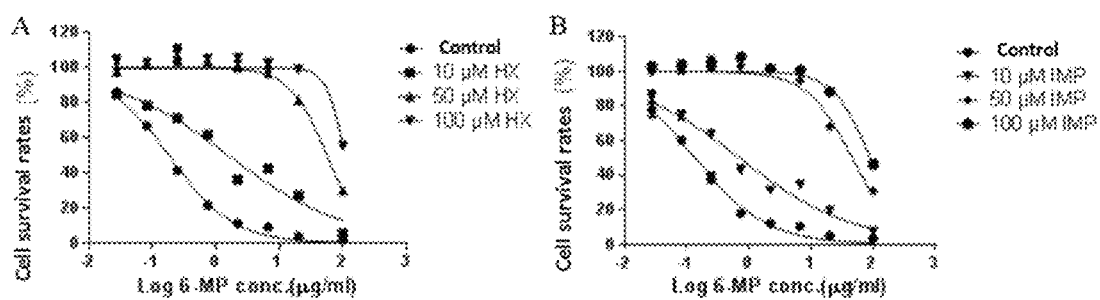
FIG. 15 Exogenous purine affects the resistance of Reh cells to chemotherapeutic drug 6-MP.

The experimental results are shown in FIG. 15. Compared with the water control, the $IC_{50}$ values of 6-MP in the cells which was added with hypoxanthine and female xanthine nucleotides were significantly increased in the experimental group, which demonstrate that the viability of cells after 6-MP treatment was significantly improved when pretreated by exogenous purine, i.e. drug resistance of Reh on 6-MP was significantly increased.

Embodiment 17

Addition of exogenous purine affects the metabolism of chemotherapeutic drug 6-MP in Reh cells.

(i) Cell inoculation: Reh cells were counted and seeded into 6 cm of culture dishes, and $3\times10^6$ cells were inoculated in each dish.

(ii) Cell treatment: 50 μM of hypoxanthine (HX) or hypoxanthine (IMP) was added into the 6 cm of culture dish for pretreating the cells for 1 hours, after that, 10 μM of chemotherapeutic drug 6-MP was added for treating the cells for 4 hours.

(iii) Cell collection: The cells were transferred to a centrifuge tube, centrifuged at 3,000 g for 5 minutes, the supernatant was removed, and the cells were lysed at a volume of 200 μl 80% methanol per $3\times10^6$ cells.

(iv) The contents of 6-MP metabolites, TIMP and TGMP, were detected by LC-MS (ABI 5500 Qtrap coupled with Waters Acquity UPLC), and standard curve quantifications were made using TIMP (Jean Bioscience, cat #NU-1148) and TGMP (Jean Bioscience, cat #NU-1121), respectively.

Figure 16:
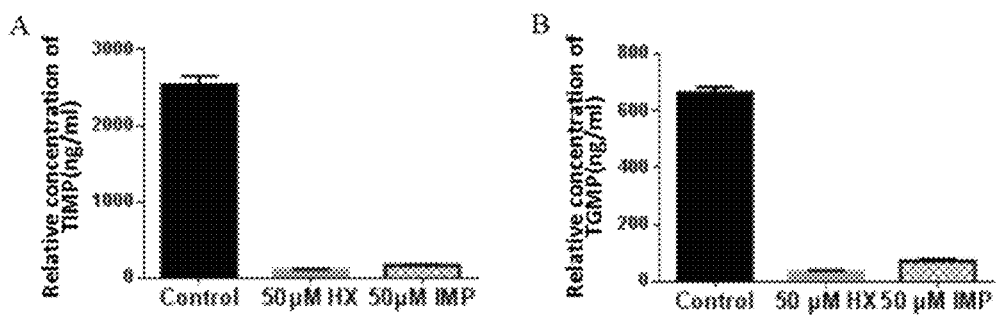
FIG. 16 Exogenous purine affects the metabolism of Reh cells to chemotherapeutic drug 6-MP.

The experimental results are shown in FIG. 16. For those Reh cells treated with exogenous purine in the experimental group, the intracellular contents of metabolites TIMP, TGMP of 6-MP were significantly decreased compared with that of control group.

Embodiment 18

Hypoxanthine competitively inhibits the response of chemotherapeutic drug 6-MP.

Figure 17:
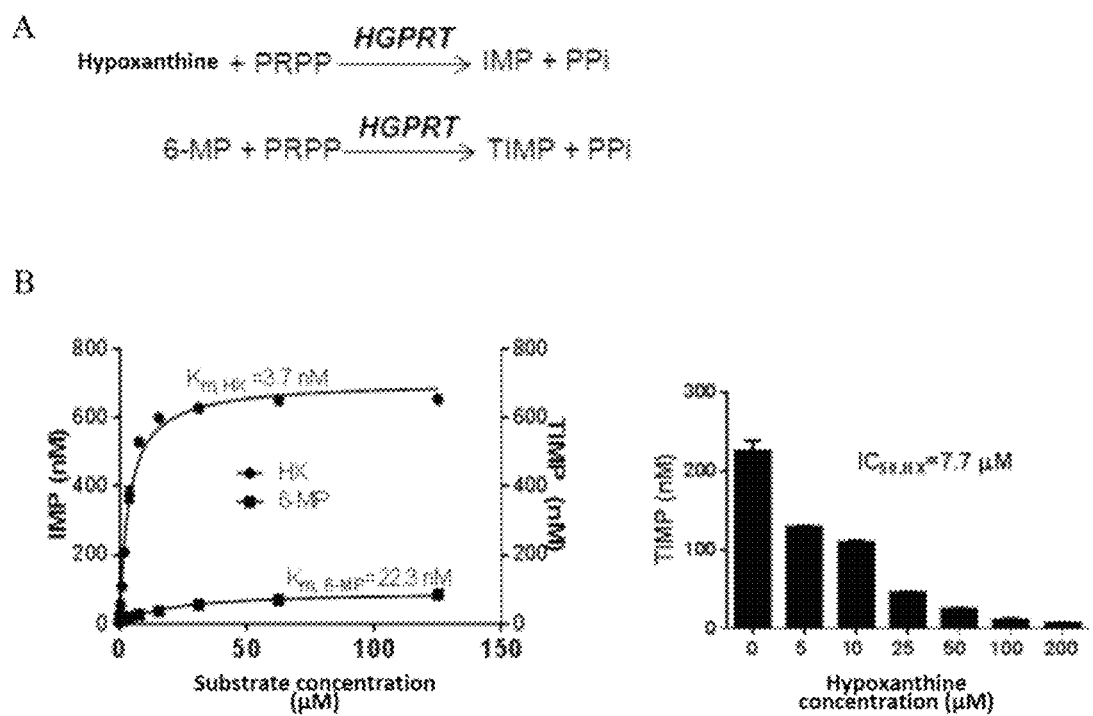
FIG. 17 Hypoxanthine competitively inhibits the effect of chemotherapeutic drug 6-MP.

Chemotherapeutic drug 6-MP is an analog of hypoxanthine, and both 6-MP and hypoxanthine are substrates of HGPRT. The present invention established an in vitro enzymatic reaction to determine the Km value of 6-MP and hypoxanthine reacting with HGPRT, respectively, which reflects the affinity of HGPRT to hypoxanthine and 6-MP. The preferred embodiment is as follows:

The establishment of in vitro enzymatic reaction is shown in FIG. 17A:

The specific reaction system is as follows:

TABLE 7

| 2*Buffer | Final concentration | Volume (μl) |
|---|---|---|
| KCl (mM) | 200 | 320 |
| Tris 8.5(mM) | 200 | 800 |
| MgCl$_2$ (mM) | 24 | 96 |
| DTT(mM) | 2 | 8 |
| BSA | 0.01 | 8 |
| H$_2$O | | 2776 |
| Total volume | | 4000 |

TABLE 8

| | Final concentration | Volume (μl) |
|---|---|---|
| HGPRT (NOVOCIB, #E-NOV9) | 0.047 | 1.74 |
| PRPP(Sigma, #P8296) | 1 | 240.0 |
| 2*Buffer | 1 | 1200.0 |
| H$_2$O | | 958.3 |
| Total volume | | 2400 |

TABLE 9

| Hypoxanthine | Final concentration(μM) | 6-MP | Final concentration (μM) |
|---|---|---|---|
| 1 | 250 | 1 | 1 |
| 2 | 125 | 2 | 0.5 |
| 3 | 62.5 | 3 | 0.25 |
| 4 | 31.25 | 4 | 0.125 |
| 5 | 15.625 | 5 | 0.0625 |
| 6 | 7.8125 | 6 | 0.03125 |
| 7 | 3.90625 | 7 | 0.015625 |
| 8 | 1.953125 | 8 | 0.0078125 |
| 9 | 0.9765625 | 9 | 0.00390625 |
| 10 | 0.48828125 | 10 | 0.001953125 |
| 11 | 0.244140625 | 11 | 0.000976563 |

Hypoxanthine and 6-MP were diluted in a concentration gradient, reacted at 37° C. for 1 hour, and 80% methanol was added to terminate the reaction. The contents of IMP and TIMP were detected by LC-MS. The reaction curves were plotted and the Km values of hypoxanthine and 6-MP were calculated by Graphpad 5.0 software.

Results As shown in FIG. 17B, the affinity of hypoxanthine and HGPRT was significantly higher than that of 6-MP and HGPRT, and when 100 μM 6-MP was used as the reaction substrate, TIMP generation has been significantly inhibited with the increased concentration of hypoxanthine.

Embodiment 19

Lometrexol Reverses the 6-MP Drug Resistance Induced by PRPS1 Gene Mutation

Lometrexol is a small molecule inhibitor of GART. The present invention detected that lo Lometrexol can reverse the 6-MP drug resistance induced by of PRPS1 gene mutation, and the specific steps are as follows:

(i) Cell inoculation: cell lines Reh-PRPS1-S103T and Reh-PRPS1-A190T were counted and seeded into 96-well plates with 10$^4$ cells inoculating in each well and five parallel wells setting up.

(ii) Cell treatment: the cells were pretreated with 5 ng/ml of Lometrexol or DMSO control, and 6-MP was diluted gradiently and added into 96-well plates plated with cells. Cells were cultured at 37° C. for 72 hours.

(iii) Reading of values: subsequently, 50 μl of CellTiter-Glo reagent (Promega) was added to each well and incubated at room temperature for 10 minutes. The chemiluminescence values were read in a microplate reader.

(iv) Calculation: IC$_{50}$ values were calculated using Graphpad 5.0 software and the differences were compare.

(v) Determining the concentration of 6-MP metabolites: the same as Embodiment 13.

(vi) Determining the intracellular concentration of hypoxanthine: the same as Embodiment 14.

The experimental results are shown in FIG. 18. Compared with the respective controls, the IC$_{50}$ values of the drug 6-MP were significantly decreased in Reh-PRPS1-S103T and Reh-PRPS1-A190T cells treated with Lometrexol, meanwhile the in vivo 6-MP metabolites TIMP and TGMP were significantly increased, indicating that Lometrexol significantly reduced the resistance of cell lines Reh-PRPS1-S103T and Reh-PRPS1-A190T to 6-MP. And the intracellular levels of 6-MP metabolites TIMP and TGMP in treated cell lines Reh-PRPS1-S103T and Reh-PRPS1-A190T were significantly increased, meanwhile the concentration of hypoxanthine was significantly decreased.

Embodiment 20

Mass spectrometry detects purine metabolites and purine analog metabolites of drugs.

Drugs and Reagents

Methanol and acetonitrile (HPLC grade) were purchased from Sigma-Aldrich (USA), formic acid (HPLC grade) was purchased from Merck (Germany), and experimental water was prepared by Millipore-Q.

Experimental Instruments

Liquid Chromatography/Mass Spectrometer (UPLC-MS/MS):

AB SCIEX QTRAP® 5500 (Singapore)

Waters Ultra Performance LC system (Singapore)
1. ACQUITY™ Binary Solvent Manager
2. ACQUITY™ Column Manager
3. ACQUITY™ Sample Organizer
4. ACQUITY™ Sample Manager Analyst, version 1.5.2 was used for data acquisition and processing systems.

Other instruments: Thermo Fisher −70° C. ultra low temperature refrigerator (USA); Eppendorf 5810R high speed, high capacity, and low temperature centrifugator (Germany); IKA Vibrax VXR (Germany); IKA Vortex (Germany); KQ5200DA ultrasonic cleaner (Kunshan) etc.

1. Method of Sample Analysis
Method of Sample Treatment

The cells were collected using 80% methanol, and then centrifuged for 5 minutes at 12,000 rpm. The supernatant was transferred to a new EP tube and 20 μl of the supernatant was taken for LC-MS/MS analysis.

1) Labeled PRPP, ADP and GDP:
Chromatographic Conditions
Mobile phase composition: mobile phase A: 50 mM ammonium bicarbonate (pH 9.5)
    Mobile phase B: acetonitrile:water=6:1 (v/v)
    Gradient elution:

TABLE 10

| Time (min) | Mobile phase B (%) |
|---|---|
| 1.00 | 90 |
| 4.00 | 5.0 |
| 5.00 | 5.0 |
| 5.10 | 90 |
| 6.00 | 90 |

Chromatographic column: apHera™ NH2 Polymer (2×150 mm);
Flow rate: 0.6 ml/min; Injection volume: 20 μl;
Detection Conditions of Mass Spectrometry Electron spray ion source (Turbo spray) was used for multi-channel reaction monitoring (MRM) mode analysis for two-stage mass spectrometry. The parameters of the mass spectrometry test and the parameters of the ion source are as follows:

TABLE 11

| Analyte | Q1 (m/z) | Q3 (m/z) | DP (V) | CE(V) |
|---|---|---|---|---|
| PRPP label | 394.0 | 177.0 | −80 | −26 |
| ADP | 426.1 | 158.9 | −110 | −31 |
| GDP | 442.1 | 78.8 | −115 | −95 |

2) IMP (labeled IMP+3 and labeled IMP+9), HX, TIMP, TGMP, AICAR, Inosine, 6-MP, 6-TG, MMP, r-MP, r-TG and r-MMP
Chromatographic Conditions
Mobile phase composition: mobile phase A: Water-0.025% formic acid-1 mM
Mobile phase B: Methanol-0.025% formic acid-1 mM ammonium acetate
Gradient elution:

TABLE 10

| Time (min) | Mobile phase B (%) |
|---|---|
| 0.40 | 2.0 |
| 1.00 | 90 |
| 2.40 | 90 |
| 2.50 | 2.0 |
| 5.50 | 2.0 |

Chromatographic column: Agilent Eclipse XDB-C18 (4.6×150 mm, 5 μm);
Flow rate: 0.6 ml/min; Injection volume: 15 μl;
Detection Condition of Mass Spectrometry Electron spray ion source (Turbo spray) was used for multi-channel reaction monitoring (MRM) mode analysis for two-stage mass spectrometry. The parameters of the mass spectrometry test and the parameters of the ion source are as follows:

TABLE 13

| Analyte | Q1 (m/z) | Q3 (m/z) | DP (V) | CE (V) |
|---|---|---|---|---|
| IMP | 347.1 | 78.7 | −125 | −80 |
| Labeled IMP + 3 | 350.1 | 78.7 | −125 | −80 |
| Labeled IMP + 9 | 356.1 | 78.7 | −125 | −80 |
| HX | 135.0 | 91.9 | −115 | −23 |
| HX + 9 | 144.0 | 99.0 | −99 | −25 |
| TIMP | 363.0 | 79.0 | −114 | −60 |
| TGMP | 378.1 | 211.0 | −100 | −26 |
| AICAR | 259.1 | 110.0 | 55 | 40 |
| Inosine | 269.1 | 137.0 | 60 | 24 |
| 6-MP | 153.2 | 119.0 | 130 | 30 |
| 6-TG | 168.0 | 82.0 | 100 | 60 |
| MMP | 167.0 | 125.0 | 150 | 35 |
| r-MP | 285.0 | 119.0 | 80 | 58 |
| r-TG | 300.0 | 168.0 | 60 | 17 |
| r-MMP | 299.2 | 167.0 | 90 | 24 |

Embodiment 21

Nucleic Acid Drugs Targeting Purine Synthesis Pathway

Preparation of lentivirus LV-shATIC, LV-shGART and LV-shPPAT for purine de novo synthesis pathway and its application in reversing 6-MP drug resistance caused by PRPS1 gene mutation.

(i) Construction of shRNA lentiviral vector: shRNA lentiviral vector GV298 for ATIC, GART and PPAT was purchased from Genechem, and DNA sequences corresponding to sequences of used shRNA were as follows:

```
shATIC-1:
                                        (SEQ ID NO: 49)
AATCTCTATCCCTTTGTAA, shATIC-2:
                                        (SEQ ID NO: 50)
TGGAATCCTAGCTCGTAAT, shGART-1:
                                        (SEQ ID NO: 51)
CCAGGAGTTTGACTTACAA, shGART-2:
                                        (SEQ ID NO: 52)
CTAACTGTTGTCATGG CAA, shPPAT-1:
                                        (SEQ ID NO: 53)
CTTCGTTGTTGAAACACTT, shPPAT-2:
                                        (SEQ ID NO: 54)
TGTCTAACTGTAGA CAAAT, shControl:
                                        (SEQ ID NO: 55)
TTCTCCGAACGTGTCACGT.
```

(ii) Cell lines Reh, Reh-PRPS1-WT, Reh-PRPS1-S103 T and Reh-PRPS1-A190T were infected respectively by control lentivirus LV-shControl, lentivirus LV-shATIC1, LV-shATIC2, LV-shGART1, LV-shGART2, LV-shPPAT1 and LV-shPPAT2 which were obtained by packaging, of which the MOI was 10, to form stable cell lines. Then 8 μg/ml of polybrene was added in, the culture medium was changed then after 24 hours, and the cells were treated with 0.8 μg/ml of puromycin for resistance selection after further cultured for 48 hours. The following stable cell lines were formed after 1 week of resistance selection: the control cell line Reh-shControl, Reh-shATIC1, Reh-shATIC2, Reh-shGART1, Reh-shGART2, Reh-shPPAT1, Reh-shPPAT2, Reh-WT-shContro, Reh-WT-shATIC1, Reh-WT-shATIC2, Reh-WT-shGART1, Reh-WT-shGART2, Reh-WT-shPPAT1, Reh-WT-shPPAT2, Reh-S103 T-shControl, Reh-S103 T-shATIC1, Reh-S103 T-shATIC2, Reh-S103 T-shGART1, Reh-S103 T-shGART2, Reh-S103 T-shPPAT1, Reh-S103 T-shPPAT2, Reh-A190T-shControl, Reh-A190T-shATIC1, Reh-A190T-shATIC2, Reh-A190T-shGART1, Reh-A190T-shGART2, Reh-A190T-shPPAT1 and Reh-A190T-shPPAT2.

(iii) Cell treatment: The drug 6-MP was diluted and added into 96-wells plate plated with cell lines as described in step (ii). Five parallel wells were set up for each cell line to detect the susceptibility of lentivirus infected cells to 6-MP. The preferred embodiment is the same as Embodiment 8.

Figure 19:
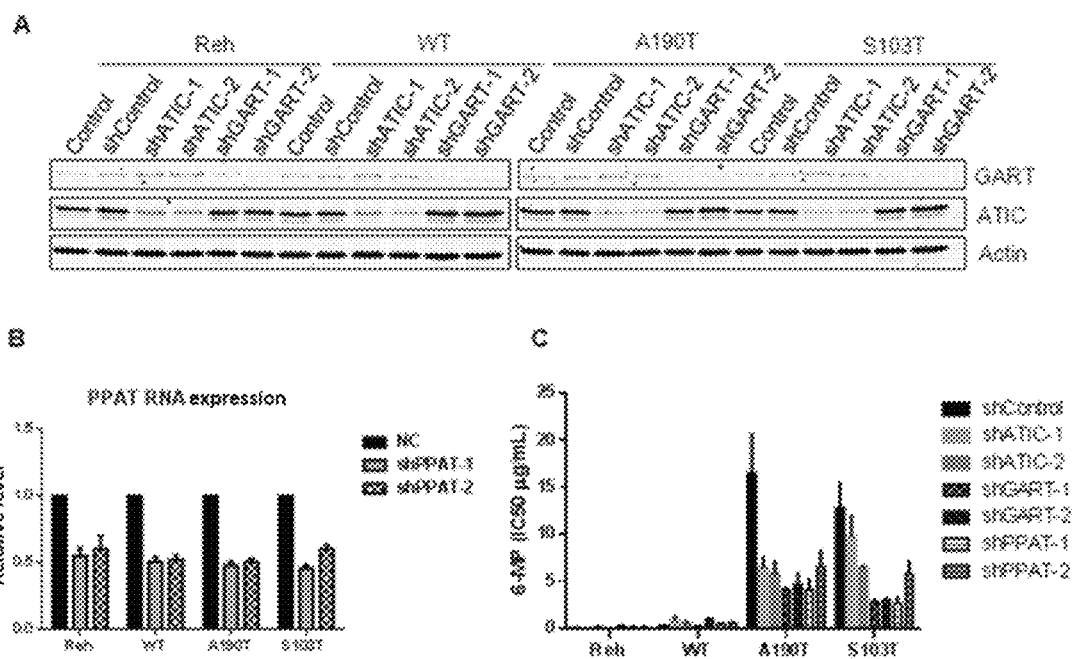
FIG. 19 Inhibitory effect of nucleic acid drug shRNA targeting to purine synthesis pathway on the drug resistance of PRPS1 S103T and A190T mutant.

As shown in FIG. 19, the 6-MP $IC_{50}$ values of cell lines Reh-S103T-shATIC1, Reh-S103 T-shATIC2, Reh-S103 T-shGART1, Reh-S103 T-shGART2, Reh-S103 T-shPPAT1, Reh-S103 T-shPPAT2, Reh-A190T-shATIC1, Reh-A190T-shATIC2, Reh-A190T-shGART1, Reh-A190T-shGART2, Reh-A190T-shPPAT1 and Reh-A190T-shPPAT2 were significantly decreased compared with the control cell line Reh-S103T-shControl and Reh-A190T-shControl infected by virus with empty load, indicating that the resistance to drug 6-MP was significantly reduced.

While the specific embodiments of the present invention have been described above, it will be understood by a person skilled in the art that these are merely illustrative examples. Accordingly, it is intended that all such alternatives, modifications, and variations which fall within the spirit and the scope of the invention be embraced by the defined claims.

What we claimed is:

1. A recombinant protein comprising a PRPS1 mutant fused to a heterologous His tag, wherein the PRPS1 mutant is formed by making amino acid substitution at any one or more of the following positions of SEQ ID NO: 2: serine is substituted by threonine at position 103, serine is substituted by asparagine at position 103, asparagine is substituted by serine at position 144, lysine is substituted by asparagine at position 176, aspartic acid is substituted by glutamic acid at position 183, alanine is substituted by threonine at position 190, leucine is substituted by phenylalanine at position 191, threonine is substituted by serine at position 303, valine is substituted by alanine at position 53, isoleucine is substituted by valine at position 72, cysteine is substituted by serine at position 77, aspartic acid is substituted by glycine at position 139, tyrosine is substituted by cysteine at position 311, serine is substituted by isoleucine at position 103, asparagine is substituted by aspartic acid at position 114 or glycine is substituted by glutamic acid at position 174.

2. A PRPS1 mutant gene, wherein the PRPS1 mutant gene encodes the recombinant protein according to claim 1.

3. The PRPS1 mutant gene according to claim 2, wherein the nucleotide sequence of said PRPS1 mutant gene comprises a nucleotide substitution at any one of the following positions of SEQ ID NO:1: G is substituted by C at position 308, G is substituted by A at position 308, A is substituted by G at position 431, G is substituted by C at position 528, C is substituted by G at position 549, G is substituted by A at position 568, G is substituted by C at position 573, C is substituted by G at position 908, T is substituted by C at position 158, A is substituted by G at position 214, G is substituted by C at position 230, A is substituted by G at position 416, A is substituted by G at position 932, G is substituted by T at position 308, A is substituted by G at position 340 or G is substituted by A at position 521.

4. A recombinant vector, wherein the recombinant vector comprises the PRPS1 mutant gene according to claim 2.

5. A transformant, wherein the transformant comprises the recombinant vector according to claim 4.

6. A PRPS1 mutant library for evaluating a risk of drug resistance and relapse of ALL, wherein said PRPS1 mutant library comprises at least a first recombinant protein comprising a first PRPS1 mutant fused to a heterologous His tag, and a second recombinant protein comprising a second PRPS1 mutant fused to a heterologous His tag, wherein each of the first PRPS1 mutant and the second PRPS1 mutant is formed by making amino acid substitution at any one or more of the following positions of SEQ ID NO: 2: serine is replaced by threonine at position 103, serine is replaced by asparagine at position 103, asparagine is replaced by serine at position 144, lysine is replaced by asparagine at position 176, aspartic acid is replaced by glutamic acid at position 183, alanine is replaced by threonine at position 190, leucine is replaced by phenylalanine at position 191, or threonine is replaced by serine at position 303.

7. The PRPS1 mutant library according to claim 6, further comprising a third recombinant protein comprising a third PRPS1 mutant fused to a heterologous His tag, wherein the third PRPS1 mutant is formed by making amino acid substitution at any one or more of the following positions of SEQ ID NO: 2: valine is replaced by alanine at position 53, isoleucine is replaced by valine at position 72, cysteine is replaced by serine at position 77, aspartic acid is replaced by glycine at position 139, tyrosine is replaced by cysteine at position 311, serine is replaced by isoleucine at position 103, asparagine is replaced by aspartic acid at position 114, glycine is replaced by glutamic acid at position 174, or alanine is replaced by valine at position 190.

8. A PRPS1 mutant gene library for evaluating a risk of drug resistance and relapse of ALL, wherein the PRPS1 mutant gene library comprises following PRPS1 mutant genes having a nucleotide sequence of SEQ ID NO: 1 according to claim 3, wherein G is replaced by C at position 308, G is replaced by A at position 308, A is replaced by G at position 431, G is replaced by C at position 528, C is replaced by G at position 549, G is replaced by A at position 568, G is replaced by C at position 573, or C is replaced by G at position 908.

9. The PRPS1 mutant gene library according to claim 8, wherein the PRPS1 mutant gene library further comprises one or more following PRPS1 mutant genes having a nucleotide sequence of SEQ ID NO: 1, wherein T is replaced by C at position 158, A is replaced by G at position 214, G is replaced by C at position 230, A is replaced by G at position 416, A is replaced by G at position 416, A is replaced by G at position 932, G is replaced by T at position 308, A is replaced by G at position 340, G is replaced by A at position 521, or C is replaced by T at position 569.

* * * * *

SEQUENCE LISTING

<160> NUMBER OF SEQ ID NOS: 54

<210> SEQ ID NO 1
<211> LENGTH: 957
<212> TYPE: DNA
<213> ORGANISM: Artificial Sequence
<220> FEATURE:
<223> OTHER INFORMATION: PRPS1 Mutant Gene

<400> SEQUENCE: 1

```
atgccgaata tcaaaatctt cagcggcagc tcccaccagg acttatctca gaaaattgct      60
gaccgcctgg gcctggagct aggcaaggtg gtgactaaga aattcagcaa ccaggagacc     120
tgtgtggaaa ttggtgaaag tgtacgtgga gaggatgtct acattgttca gagtggttgt     180
ggcgaaatca atgacaattt aatggagctt ttgatcatga ttaatgcctg caagattgct     240
tcagccagcc gggttactgc agtcatccca tgcttccctt atgcccggca ggataagaaa     300
gataagagcc gggcgccaat ctcagccaag cttgttgcaa atatgctatc tgtagcaggt     360
gcagatcata ttatcaccat ggacctacat gcttctcaaa ttcagggctt tttttgatatc     420 ccagtagaca atttgtatgc agagccggct gtcctaaagt ggataaggga gaatatctct     480
gagtggagga actgcactat tgtctcacct gatgctggtg gagctaagag agtgacctcc     540
attgcagaca ggctgaatgt ggactttgcc ttgattcaca agaacggaa gaaggccaat     600 gaagtggacc gcatggtgct tgtgggagat gtgaaggatc gggtggccat ccttgtggat     660
gacatggctg acacttgtgg cacaatctgc catgcagctg acaaacttct ctcagctggc     720
gccaccagag tttatgccat cttgactcat ggaatcttct ccggtcctgc tatttctcgc     780
atcaacaacg catgctttga ggcagtagta gtcaccaata ccataccctca ggaggacaag     840 atgaagcatt gctccaaaat acaggtgatt gacatctcta tgatccttgc agaagccatc     900
aggagaactc acaatggaga atccgtttct tacctattca gccatgtccc tttataa       957
```

<210> SEQ ID NO 2
<211> LENGTH: 318
<212> TYPE: PRT
<213> ORGANISM: Homo sapiens

<400> SEQUENCE: 2

Met Pro Asn Ile Lys Ile Phe Ser Gly Ser Ser His Gln Asp Leu Ser
1               5                   10                  15

Gln Lys Ile Ala Asp Arg Leu Gly Leu Glu Leu Gly Lys Val Val Thr
            20                  25                  30

Lys Lys Phe Ser Asn Gln Glu Thr Cys Val Glu Ile Gly Glu Ser Val
        35                  40                  45

-continued

```
Arg Gly Glu Asp Val Tyr Ile Val Gln Ser Gly Cys Gly Glu Ile Asn
     50                  55                  60

Asp Asn Leu Met Glu Leu Leu Ile Met Ile Asn Ala Cys Lys Ile Ala
 65                  70                  75                  80

Ser Ala Ser Arg Val Thr Ala Val Ile Pro Cys Phe Pro Tyr Ala Arg
                 85                  90                  95

Gln Asp Lys Lys Asp Lys Ser Arg Ala Pro Ile Ser Ala Lys Leu Val
                100                 105                 110

Ala Asn Met Leu Ser Val Ala Gly Ala Asp His Ile Ile Thr Met Asp
            115                 120                 125

Leu His Ala Ser Gln Ile Gln Gly Phe Phe Asp Ile Pro Val Asp Asn
            130                 135                 140

Leu Tyr Ala Glu Pro Ala Val Leu Lys Trp Ile Arg Glu Asn Ile Ser
145                 150                 155                 160

Glu Trp Arg Asn Cys Thr Ile Val Ser Pro Asp Ala Gly Gly Ala Lys
                165                 170                 175

Arg Val Thr Ser Ile Ala Asp Arg Leu Asn Val Asp Phe Ala Leu Ile
            180                 185                 190

His Lys Glu Arg Lys Ala Asn Glu Val Asp Arg Met Val Leu Val
            195                 200                 205

Gly Asp Val Lys Asp Arg Val Ala Ile Leu Val Asp Asp Met Ala Asp
    210                 215                 220

Thr Cys Gly Thr Ile Cys His Ala Ala Asp Lys Leu Leu Ser Ala Gly
225                 230                 235                 240

Ala Thr Arg Val Tyr Ala Ile Leu Thr His Gly Ile Phe Ser Gly Pro
                245                 250                 255

Ala Ile Ser Arg Ile Asn Asn Ala Cys Phe Glu Ala Val Val Val Thr
            260                 265                 270

Asn Thr Ile Pro Gln Glu Asp Lys Met Lys His Cys Ser Lys Ile Gln
            275                 280                 285

Val Ile Asp Ile Ser Met Ile Leu Ala Glu Ala Ile Arg Arg Thr His
    290                 295                 300

Asn Gly Glu Ser Val Ser Tyr Leu Phe Ser His Val Pro Leu
305                 310                 315

<210> SEQ ID NO 3
<211> LENGTH: 19
<212> TYPE: DNA
<213> ORGANISM: Artificial Sequence
<220> FEATURE:
<223> OTHER INFORMATION: Forward primer of exon 1 of PRPS1

<400> SEQUENCE: 3
tgagtctgtg gccgacttc                                              19

<210> SEQ ID NO 4
<211> LENGTH: 20
<212> TYPE: DNA
<213> ORGANISM: Artificial Sequence
<220> FEATURE:
<223> OTHER INFORMATION: Reverse primer of exon 1 of PRPS1

<400> SEQUENCE: 4
cgaccccatc cctcctatac                                             20

<210> SEQ ID NO 5
<211> LENGTH: 22
```

```
<212> TYPE: DNA
<213> ORGANISM: Artificial Sequence
<220> FEATURE:
<223> OTHER INFORMATION: Forward primer of exon 2 of PRPS1

<400> SEQUENCE: 5
tcaatccaca cttggttgaa tc                                              22

<210> SEQ ID NO 6
<211> LENGTH: 21
<212> TYPE: DNA
<213> ORGANISM: Artificial Sequence
<220> FEATURE:
<223> OTHER INFORMATION: Reverse primer of exon 2 of PRPS1

<400> SEQUENCE: 6
tccagaggag ttggtgctta g                                               21

<210> SEQ ID NO 7
<211> LENGTH: 23
<212> TYPE: DNA
<213> ORGANISM: Artificial Sequence
<220> FEATURE:
<223> OTHER INFORMATION: Forward primer of exon 3 of PRPS1

<400> SEQUENCE: 7
atgaatttct gggtaccata gtg                                             23

<210> SEQ ID NO 8
<211> LENGTH: 22
<212> TYPE: DNA
<213> ORGANISM: Artificial Sequence
<220> FEATURE:
<223> OTHER INFORMATION: Reverse primer of exon 3 of PRPS1

<400> SEQUENCE: 8
cttctctgca gtcttcagca tc                                              22

<210> SEQ ID NO 9
<211> LENGTH: 20
<212> TYPE: DNA
<213> ORGANISM: Artificial Sequence
<220> FEATURE:
<223> OTHER INFORMATION: Forward primer of exon 4 of PRPS1

<400> SEQUENCE: 9
aatctaccac actgggcctg                                                 20

<210> SEQ ID NO 10
<211> LENGTH: 23
<212> TYPE: DNA
<213> ORGANISM: Artificial Sequence
<220> FEATURE:
<223> OTHER INFORMATION: Reverse primer of exon 4 of PRPS1

<400> SEQUENCE: 10
ccatgtgcta gctacttaca tcc                                             23

<210> SEQ ID NO 11
<211> LENGTH: 18
<212> TYPE: DNA
<213> ORGANISM: Artificial Sequence
<220> FEATURE:
<223> OTHER INFORMATION: Forward primer of exon 5 of PRPS1

<400> SEQUENCE: 11
```

```
ccccggcctc tttagtcc                                                 18

<210> SEQ ID NO 12
<211> LENGTH: 20
<212> TYPE: DNA
<213> ORGANISM: Artificial Sequence
<220> FEATURE:
<223> OTHER INFORMATION: Reverse primer of exon 5 of PRPS1

<400> SEQUENCE: 12
tcagcaggct gaagacattc                                               20

<210> SEQ ID NO 13
<211> LENGTH: 20
<212> TYPE: DNA
<213> ORGANISM: Artificial Sequence
<220> FEATURE:
<223> OTHER INFORMATION: Forward primer of exon 6 of PRPS1

<400> SEQUENCE: 13
gttgtggaag cctaagcagg                                               20

<210> SEQ ID NO 14
<211> LENGTH: 24
<212> TYPE: DNA
<213> ORGANISM: Artificial Sequence
<220> FEATURE:
<223> OTHER INFORMATION: Reverse primer of exon 6 of PRPS1

<400> SEQUENCE: 14
cttcagaatc cagagaccta attc                                          24

<210> SEQ ID NO 15
<211> LENGTH: 20
<212> TYPE: DNA
<213> ORGANISM: Artificial Sequence
<220> FEATURE:
<223> OTHER INFORMATION: Forward primer of exon 7 of PRPS1

<400> SEQUENCE: 15
tcatgacagg gaaacagcac                                               20

<210> SEQ ID NO 16
<211> LENGTH: 20
<212> TYPE: DNA
<213> ORGANISM: Artificial Sequence
<220> FEATURE:
<223> OTHER INFORMATION: Reverse primer of exon 7 of PRPS1

<400> SEQUENCE: 16
gagcttcccc agtcacagtc                                               20

<210> SEQ ID NO 17
<211> LENGTH: 35
<212> TYPE: DNA
<213> ORGANISM: Artificial Sequence
<220> FEATURE:
<223> OTHER INFORMATION: Forward primer of prokaryotic expression vector
      of PRPS1

<400> SEQUENCE: 17
cgcggcagcc atatgccgaa tatcaaaatc ttcag                              35

<210> SEQ ID NO 18
<211> LENGTH: 42
<212> TYPE: DNA
```

<213> ORGANISM: Artificial Sequence
<220> FEATURE:
<223> OTHER INFORMATION: Reverse primer of prokaryotic expression vector
      of PRPS1

<400> SEQUENCE: 18
gtggtggtgc tcgagttata aagggacatg gctgaatagg ta                42

<210> SEQ ID NO 19
<211> LENGTH: 45
<212> TYPE: DNA
<213> ORGANISM: Artificial Sequence
<220> FEATURE:
<223> OTHER INFORMATION: Forward primer of eukaryotic expression vector
      of PRPS1

<400> SEQUENCE: 19
gaggatcccc gggtaccggt cgccaccatg ccgaatatca aaatc             45

<210> SEQ ID NO 20
<211> LENGTH: 46
<212> TYPE: DNA
<213> ORGANISM: Artificial Sequence
<220> FEATURE:
<223> OTHER INFORMATION: Reverse primer of eukaryotic expression vector
      of PRPS1

<400> SEQUENCE: 20
tccttgtagt ccataccgtg gtggtggtgg tggtgctcga gtaaag            46

<210> SEQ ID NO 21
<211> LENGTH: 31
<212> TYPE: DNA
<213> ORGANISM: Artificial Sequence
<220> FEATURE:
<223> OTHER INFORMATION: Forward primer of mutation S103T

<400> SEQUENCE: 21
gaaagataag acccgggcgc caatctcagc c                            31

<210> SEQ ID NO 22
<211> LENGTH: 30
<212> TYPE: DNA
<213> ORGANISM: Artificial Sequence
<220> FEATURE:
<223> OTHER INFORMATION: Reverse primer of mutation S103T

<400> SEQUENCE: 22
ggcgcccggg tcttatcttt cttatcctgc                              30

<210> SEQ ID NO 23
<211> LENGTH: 31
<212> TYPE: DNA
<213> ORGANISM: Artificial Sequence
<220> FEATURE:
<223> OTHER INFORMATION: Forward primer of mutation S103N

<400> SEQUENCE: 23
gaaagataag aaccgggcgc caatctcagc c                            31

<210> SEQ ID NO 24
<211> LENGTH: 30
<212> TYPE: DNA
<213> ORGANISM: Artificial Sequence
<220> FEATURE:
<223> OTHER INFORMATION: Reverse primer of mutation S103N

<400> SEQUENCE: 24
ggcgcccggt tcttatcttt cttatcctgc                                30

<210> SEQ ID NO 25
<211> LENGTH: 33
<212> TYPE: DNA
<213> ORGANISM: Artificial Sequence
<220> FEATURE:
<223> OTHER INFORMATION: Forward primer of mutation N144S

<400> SEQUENCE: 25
gcatacaaac tgtctactgg gatacaaaaa aag                             33

<210> SEQ ID NO 26
<211> LENGTH: 30
<212> TYPE: DNA
<213> ORGANISM: Artificial Sequence
<220> FEATURE:
<223> OTHER INFORMATION: Forward primer of mutation T303S

<400> SEQUENCE: 26
catcaggaga agtcacaatg gagaatccgt                                 30

<210> SEQ ID NO 27
<211> LENGTH: 29
<212> TYPE: DNA
<213> ORGANISM: Artificial Sequence
<220> FEATURE:
<223> OTHER INFORMATION: Reverse primer of mutation T303S

<400> SEQUENCE: 27
ccattgtgac ttctcctgat ggcttctgc                                  29

<210> SEQ ID NO 28
<211> LENGTH: 26
<212> TYPE: DNA
<213> ORGANISM: Artificial Sequence
<220> FEATURE:
<223> OTHER INFORMATION: Forward primer of mutation K176N

<400> SEQUENCE: 28
ggagctaaca gagtgacctc cattgc                                     26

<210> SEQ ID NO 29
<211> LENGTH: 26
<212> TYPE: DNA
<213> ORGANISM: Artificial Sequence
<220> FEATURE:
<223> OTHER INFORMATION: Reverse primer of mutation K176N

<400> SEQUENCE: 29
gtcactctgt tagctccacc agcatc                                     26

<210> SEQ ID NO 30
<211> LENGTH: 31
<212> TYPE: DNA
<213> ORGANISM: Artificial Sequence
<220> FEATURE:
<223> OTHER INFORMATION: Forward primer of mutation D183E

<400> SEQUENCE: 30
ccattgcaga gaggctgaat gtggactttg c                               31

<210> SEQ ID NO 31
<211> LENGTH: 30

```
<212> TYPE: DNA
<213> ORGANISM: Artificial Sequence
<220> FEATURE:
<223> OTHER INFORMATION: Reverse primer of mutation D183E

<400> SEQUENCE: 31
cattcagcct ctctgcaatg gaggtcactc                                              30

<210> SEQ ID NO 32
<211> LENGTH: 31
<212> TYPE: DNA
<213> ORGANISM: Artificial Sequence
<220> FEATURE:
<223> OTHER INFORMATION: Forward primer of mutation A190T

<400> SEQUENCE: 32
gtggacttta ccttgattca caaagaacgg a                                            31

<210> SEQ ID NO 33
<211> LENGTH: 31
<212> TYPE: DNA
<213> ORGANISM: Artificial Sequence
<220> FEATURE:
<223> OTHER INFORMATION: Reverse primer of mutation A190T

<400> SEQUENCE: 33
gtgaatcaag gtaaagtcca cattcagcct g                                            31

<210> SEQ ID NO 34
<211> LENGTH: 31
<212> TYPE: DNA
<213> ORGANISM: Artificial Sequence
<220> FEATURE:
<223> OTHER INFORMATION: Forward primer of mutation A190V

<400> SEQUENCE: 34
gtggactttg tcttgattca caaagaacgg a                                            31

<210> SEQ ID NO 35
<211> LENGTH: 31
<212> TYPE: DNA
<213> ORGANISM: Artificial Sequence
<220> FEATURE:
<223> OTHER INFORMATION: Reverse primer of mutation A190V

<400> SEQUENCE: 35
gtgaatcaag acaaagtcca cattcagcct g                                            31

<210> SEQ ID NO 36
<211> LENGTH: 31
<212> TYPE: DNA
<213> ORGANISM: Artificial Sequence
<220> FEATURE:
<223> OTHER INFORMATION: Forward primer of mutation L191F

<400> SEQUENCE: 36
gtggactttg ccttcattca caaagaacgg a                                            31

<210> SEQ ID NO 37
<211> LENGTH: 31
<212> TYPE: DNA
<213> ORGANISM: Artificial Sequence
<220> FEATURE:
<223> OTHER INFORMATION: Reverse primer of mutation L191F

<400> SEQUENCE: 37
```
gtgaatgaag gcaaagtcca cattcagcct g                                         31

<210> SEQ ID NO 38
<211> LENGTH: 20
<212> TYPE: DNA
<213> ORGANISM: Homo sapiens

<400> SEQUENCE: 38
gcagcccgag tacttataat                                                      20

<210> SEQ ID NO 39
<211> LENGTH: 20
<212> TYPE: DNA
<213> ORGANISM: Homo sapiens

<400> SEQUENCE: 39
tgaatctggt cgcttccgga                                                      20

<210> SEQ ID NO 40
<211> LENGTH: 96
<212> TYPE: RNA
<213> ORGANISM: Artificial Sequence
<220> FEATURE:
<223> OTHER INFORMATION: GART guide RNA

<400> SEQUENCE: 40
gcagcccgag uacuuauaau guuuuagagc uagaaauagc aaguuaaaau aaggcuaguc          60
cguuaucaac uugaaaaagu ggcaccgagu cggugc                                    96

<210> SEQ ID NO 41
<211> LENGTH: 96
<212> TYPE: RNA
<213> ORGANISM: Artificial Sequence
<220> FEATURE:
<223> OTHER INFORMATION: ATIC guide RNA

<400> SEQUENCE: 41
ugaaucuggu cgcuuccgga guuuuagagc uagaaauagc aaguuaaaau aaggcuaguc          60
cguuaucaac uugaaaaagu ggcaccgagu cggugc                                    96

<210> SEQ ID NO 42
<211> LENGTH: 96
<212> TYPE: RNA
<213> ORGANISM: Artificial Sequence
<220> FEATURE:
<223> OTHER INFORMATION: ATIC guide RNA

<400> SEQUENCE: 42
ugaaucuggu cgcuuccgga guuuuagagc uagaaauagc aaguuaaaau aaggcuaguc          60
cguuaucaac uugaaaaagu ggcaccgagu cggugc                                    96

<210> SEQ ID NO 43
<211> LENGTH: 96
<212> TYPE: RNA
<213> ORGANISM: Artificial Sequence
<220> FEATURE:
<223> OTHER INFORMATION: ATIC guide RNA

<400> SEQUENCE: 43
ugaaucuggu cgcuuccgga guuuuagagc uagaaauagc aaguuaaaau aaggcuaguc          60
cguuaucaac uugaaaaagu ggcaccgagu cggugc                                    96

```
<210> SEQ ID NO 44
<211> LENGTH: 96
<212> TYPE: RNA
<213> ORGANISM: Artificial Sequence
<220> FEATURE:
<223> OTHER INFORMATION: ATIC guide RNA

<400> SEQUENCE: 44
ugaaucuggu cgcuuccgga guuuuagagc uagaaauagc aaguuaaaau aaggcuaguc    60
cguuaucaac uugaaaaagu ggcaccgagu cggugc                              96

<210> SEQ ID NO 45
<211> LENGTH: 96
<212> TYPE: RNA
<213> ORGANISM: Artificial Sequence
<220> FEATURE:
<223> OTHER INFORMATION: ATIC guide RNA

<400> SEQUENCE: 45
ugaaucuggu cgcuuccgga guuuuagagc uagaaauagc aaguuaaaau aaggcuaguc    60
cguuaucaac uugaaaaagu ggcaccgagu cggugc                              96

<210> SEQ ID NO 46
<211> LENGTH: 96
<212> TYPE: RNA
<213> ORGANISM: Artificial Sequence
<220> FEATURE:
<223> OTHER INFORMATION: ATIC guide RNA

<400> SEQUENCE: 46
ugaaucuggu cgcuuccgga guuuuagagc uagaaauagc aaguuaaaau aaggcuaguc    60
cguuaucaac uugaaaaagu ggcaccgagu cggugc                              96

<210> SEQ ID NO 47
<211> LENGTH: 96
<212> TYPE: RNA
<213> ORGANISM: Artificial Sequence
<220> FEATURE:
<223> OTHER INFORMATION: ATIC guide RNA

<400> SEQUENCE: 47
ugaaucuggu cgcuuccgga guuuuagagc uagaaauagc aaguuaaaau aaggcuaguc    60
cguuaucaac uugaaaaagu ggcaccgagu cggugc                              96

<210> SEQ ID NO 48
<211> LENGTH: 19
<212> TYPE: DNA
<213> ORGANISM: Artificial Sequence
<220> FEATURE:
<223> OTHER INFORMATION: shATIC1

<400> SEQUENCE: 48
aatctctatc cctttgtaa                                                 19

<210> SEQ ID NO 49
<211> LENGTH: 19
<212> TYPE: DNA
<213> ORGANISM: Artificial Sequence
<220> FEATURE:
<223> OTHER INFORMATION: shATIC2

<400> SEQUENCE: 49
tggaatccta gctcgtaat                                                 19
```

```
<210> SEQ ID NO 50
<211> LENGTH: 19
<212> TYPE: DNA
<213> ORGANISM: Artificial Sequence
<220> FEATURE:
<223> OTHER INFORMATION: shGART1

<400> SEQUENCE: 50
ccaggagttt gacttacaa                                               19

<210> SEQ ID NO 51
<211> LENGTH: 19
<212> TYPE: DNA
<213> ORGANISM: Artificial Sequence
<220> FEATURE:
<223> OTHER INFORMATION: shGART2

<400> SEQUENCE: 51
ctaactgttg tcatggcaa                                               19

<210> SEQ ID NO 52
<211> LENGTH: 19
<212> TYPE: DNA
<213> ORGANISM: Artificial Sequence
<220> FEATURE:
<223> OTHER INFORMATION: shPPAT1

<400> SEQUENCE: 52
cttcgttgtt gaaacactt                                               19

<210> SEQ ID NO 53
<211> LENGTH: 19
<212> TYPE: DNA
<213> ORGANISM: Artificial Sequence
<220> FEATURE:
<223> OTHER INFORMATION: shPPAT2

<400> SEQUENCE: 53
tgtctaactg tagacaaat                                               19

<210> SEQ ID NO 54
<211> LENGTH: 19
<212> TYPE: DNA
<213> ORGANISM: Artificial Sequence
<220> FEATURE:
<223> OTHER INFORMATION: shControl

<400> SEQUENCE: 54
ttctccgaac gtgtcacgt                                               19
```